US012589230B2

(12) United States Patent
Andersen et al.

(10) Patent No.: US 12,589,230 B2
(45) Date of Patent: Mar. 31, 2026

(54) IMPLANTABLE PORT PLACEMENT SYSTEM INCLUDING LOW-SCARRING EXTERIOR

(71) Applicant: Bard Peripheral Vascular, Inc., Franklin Lakes, NJ (US)

(72) Inventors: Christian Andersen, Queen Creek, AZ (US); Jason R. Stats, Layton, UT (US); Trent Parry, Sandy, UT (US); Jennifer C. Woo, Sandy, UT (US); Bryon Ray Densley, Rochester, MN (US)

(73) Assignee: Bard Peripheral Vascular, Inc., Franklin Lakes, NJ (US)

( * ) Notice: Subject to any disclaimer, the term of this patent is extended or adjusted under 35 U.S.C. 154(b) by 880 days.

(21) Appl. No.: 17/264,256

(22) PCT Filed: Aug. 2, 2019

(86) PCT No.: PCT/US2019/044966
§ 371 (c)(1),
(2) Date: Jan. 28, 2021

(87) PCT Pub. No.: WO2020/028847
PCT Pub. Date: Feb. 6, 2020

(65) Prior Publication Data
US 2021/0290923 A1 Sep. 23, 2021

Related U.S. Application Data

(60) Provisional application No. 62/743,434, filed on Oct. 9, 2018, provisional application No. 62/743,419, filed (Continued)

(51) Int. Cl.
*A61M 39/02* (2006.01)
*A61M 39/00* (2006.01)

(52) U.S. Cl.
CPC . *A61M 39/0208* (2013.01); *A61M 2039/0045* (2013.01); *A61M 2039/0072* (2013.01); *A61M 2039/0238* (2013.01)

(58) Field of Classification Search
CPC ...... A61M 39/0208; A61M 2039/0232; A61M 2039/0223; A61M 2039/0226;
(Continued)

(56) References Cited

U.S. PATENT DOCUMENTS 341,473 A 5/1886 Green
4,751,926 A * 6/1988 Sasaki ................... A61B 90/00
606/108

(Continued)

FOREIGN PATENT DOCUMENTS

EP 0260080 A2 3/1988
EP 1736202 A1 12/2006
(Continued)

OTHER PUBLICATIONS

PCT/US2019/044966 filed Aug. 2, 2019 International Preliminary Report on Patentability dated Feb. 2, 2021.
(Continued)

*Primary Examiner* — Kevin C Sirmons
*Assistant Examiner* — Leah J Swanson
(74) *Attorney, Agent, or Firm* — Rutan & Tucker LLP

(57) ABSTRACT

A system and a method for streamlining the port placement process. The placement system can simultaneously form an incision, dissect tissue, create a tissue pocket of the correct size for the port being placed, and place the port subcutaneously. In an embodiment, the port includes tunneling features for creating a subcutaneous tissue pocket. In an embodiment, the insertion tool includes tunneling features for creating a subcutaneous tissue pocket. Further, the port includes a reinforced, concave septum that allows for a low
(Continued)

Figure 1A:
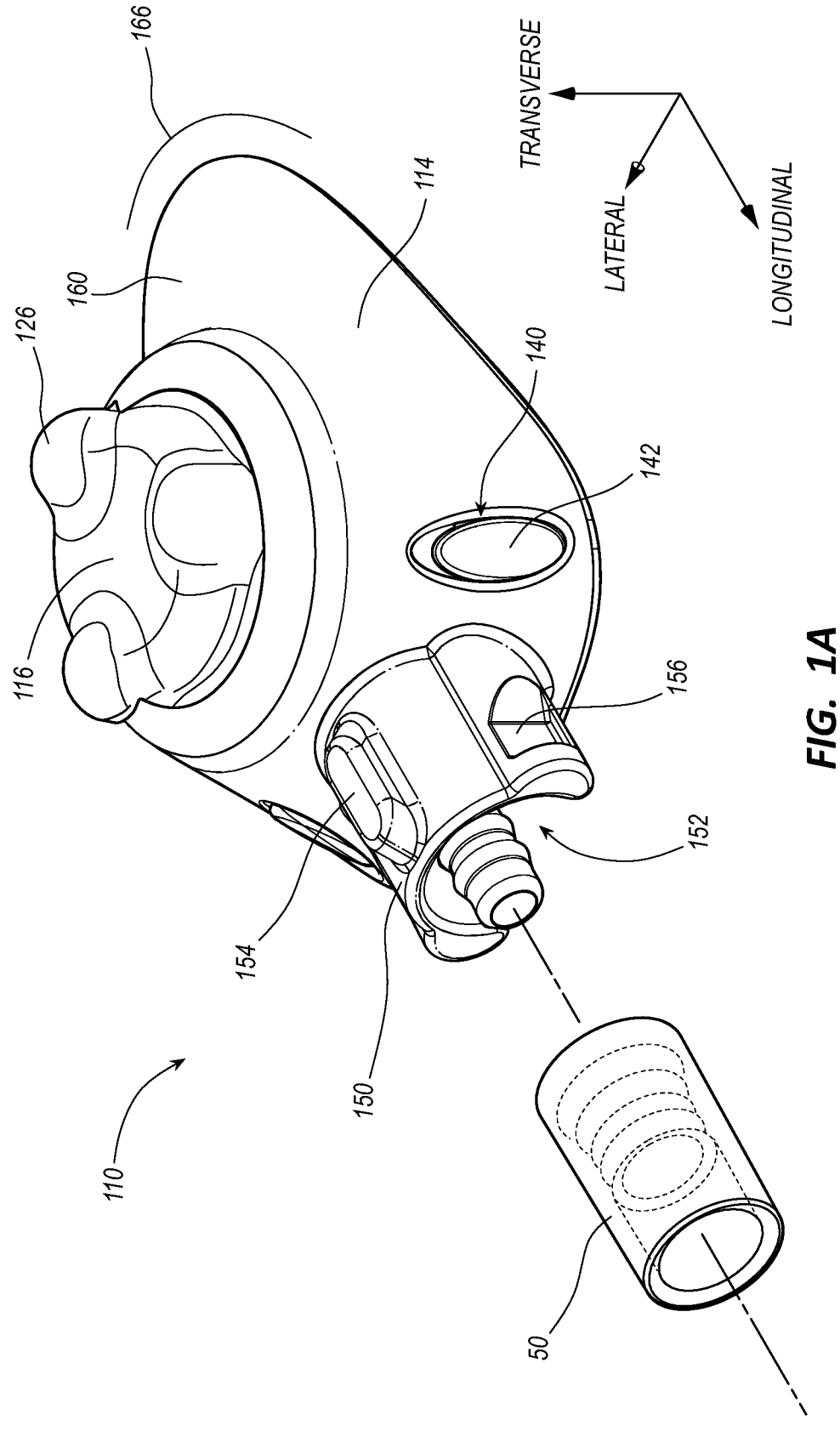

overall profile of the port, while still capable of withstanding power injection. This results in reduced procedure times, reduced scarring, and minimized wound management.

22 Claims, 16 Drawing Sheets

Related U.S. Application Data on Oct. 9, 2018, provisional application No. 62/713,968, filed on Aug. 2, 2018.

(58) Field of Classification Search
CPC .. A61M 2039/0235; A61M 2039/0238; A61M 2039/0244; A61M 2039/0045; A61M 2039/0072; A61M 2039/0291; A61M 5/14276; A61M 2039/0036; A61M 2039/0054; A61M 2039/0084; A61M 2039/009; A61M 39/02; A61M 39/0247; A61M 2039/0294; A61M 2039/0202; A61M 2039/0205; A61M 2039/0211; A61M 2039/0214; A61M 2039/0217; A61M 2039/022; A61M 2039/0229; A61M 2039/0241; A61M 2039/025; A61M 2039/0252; A61M 2039/0255; A61M 2039/0258; A61M 2039/0261; A61M 2039/0264; A61M 2039/0267; A61M 2039/027; A61M 2039/0273; A61M 2039/0276; A61M 2039/0279; A61M 2039/0282; A61M 2039/0285; A61M 2039/0288; A61M 2039/0297; A61M 2209/04; A61M 2209/045
See application file for complete search history.

(56) References Cited

U.S. PATENT DOCUMENTS

| | | | | |
|---|---|---|---|---|
| 4,781,680 | A * | 11/1988 | Redmond | A61M 39/0208 604/86 |
| 4,857,053 | A * | 8/1989 | Dalton | A61M 39/0208 604/288.02 |
| 5,137,529 | A * | 8/1992 | Watson | A61M 39/0208 604/8 |
| 5,147,483 | A | 9/1992 | Melsky et al. | |
| 5,743,873 | A | 4/1998 | Cai et al. | |
| 5,792,104 | A | 8/1998 | Speckman et al. | |
| 5,833,654 | A | 11/1998 | Powers et al. | |
| 5,919,160 | A * | 7/1999 | Sanfilippo, II | A61M 39/0208 604/93.01 |
| 5,951,512 | A | 9/1999 | Dalton | |
| 5,989,216 | A | 11/1999 | Johnson et al. | |
| 6,213,973 | B1 * | 4/2001 | Eliasen | A61M 39/0208 604/93.01 |
| 6,258,058 | B1 | 7/2001 | Sanfilippo, II | |
| 6,613,013 | B2 | 9/2003 | Haarala et al. | |
| 7,445,614 | B2 * | 11/2008 | Bunodiere | A61M 39/0208 604/288.04 |
| 7,699,821 | B2 | 4/2010 | Nowak | |
| 7,972,314 | B2 | 7/2011 | Bizup et al. | |
| 8,007,479 | B2 | 8/2011 | Birk et al. | |
| 8,021,324 | B2 | 9/2011 | Bizup et al. | |
| 8,075,536 | B2 * | 12/2011 | Gray | A61M 39/0208 604/288.04 |
| 8,092,435 | B2 | 1/2012 | Beling et al. | |
| 8,177,762 | B2 | 5/2012 | Beasley et al. | |
| 8,257,325 | B2 | 9/2012 | Schweikert et al. | |
| 8,608,712 | B2 | 12/2013 | Bizup et al. | |
| 8,852,160 | B2 | 10/2014 | Schweikert et al. | |
| 8,876,788 | B2 | 11/2014 | Glenn | |
| 8,920,390 | B2 | 12/2014 | Dalton et al. | |
| 8,926,573 | B2 | 1/2015 | Smith et al. | |
| 8,932,271 | B2 | 1/2015 | Hamatake et al. | |
| 8,992,415 | B2 | 3/2015 | Deuel et al. | |
| 9,011,388 | B2 | 4/2015 | Schwartz et al. | |
| 9,023,062 | B2 * | 5/2015 | Franklin | A61M 39/0208 606/139 |
| 9,227,045 | B2 | 1/2016 | Stats | |
| 9,327,106 | B2 | 5/2016 | Beling et al. | |
| 9,504,815 | B2 | 11/2016 | Bizup | |
| 9,517,329 | B2 | 12/2016 | Bizup et al. | |
| 9,533,133 | B2 | 1/2017 | Schweikert et al. | |
| 9,561,358 | B2 * | 2/2017 | Linden | A61M 39/0208 |
| 9,610,432 | B2 | 4/2017 | Zinn | |
| 9,707,339 | B2 | 7/2017 | Chartrand et al. | |
| 9,731,104 | B2 | 8/2017 | Linden et al. | |
| 9,950,150 | B2 | 4/2018 | Beling et al. | |
| 10,022,094 | B2 | 7/2018 | Kerr et al. | |
| 10,632,295 | B2 | 4/2020 | Bourne et al. | |
| 10,874,842 | B2 | 12/2020 | Bizup et al. | |
| 10,912,935 | B2 | 2/2021 | Wiley et al. | |
| 10,926,075 | B2 | 2/2021 | Beling et al. | |
| 10,933,625 | B2 | 3/2021 | Fisher et al. | |
| 10,940,290 | B2 | 3/2021 | Singh et al. | |
| 10,940,302 | B2 | 3/2021 | Achard de la Vente | |
| 2004/0199129 | A1 | 10/2004 | DiMatteo | |
| 2006/0293626 | A1 | 12/2006 | Byrum et al. | |
| 2007/0233017 | A1 | 10/2007 | Zinn et al. | |
| 2009/0221976 | A1 * | 9/2009 | Linden | A61M 39/0208 604/288.01 |
| 2009/0259187 | A1 * | 10/2009 | Egle | A61M 39/0208 604/257 |
| 2010/0010454 | A1 * | 1/2010 | Marshall | A61M 5/3202 604/208 |
| 2011/0034886 | A1 | 2/2011 | Elbe et al. | |
| 2011/0054407 | A1 | 3/2011 | Olroyd et al. | |
| 2011/0160673 | A1 * | 6/2011 | Magalich | A61M 39/0208 604/175 |
| 2015/0100032 | A1 | 4/2015 | Finberg et al. | |
| 2015/0343192 | A1 * | 12/2015 | Nagao | A61M 39/0208 604/288.02 |
| 2016/0081849 | A1 * | 3/2016 | Tsai | A61M 5/2053 604/290 |
| 2016/0175575 | A1 | 6/2016 | Tallarida et al. | |
| 2017/0043152 | A1 | 2/2017 | Bizup | |
| 2017/0056638 | A1 | 3/2017 | Schweikert et al. | |
| 2018/0214679 | A1 | 8/2018 | Jho | |
| 2018/0214680 | A1 | 8/2018 | Jho et al. | |
| 2018/0326196 | A1 | 11/2018 | Schweikert et al. | |
| 2020/0038644 | A1 | 2/2020 | Zinn et al. | |
| 2021/0085946 | A1 | 3/2021 | Achard de la Vente | |
| 2021/0093847 | A1 | 4/2021 | Bizup et al. | |

FOREIGN PATENT DOCUMENTS

| | | |
|---|---|---|
| WO | 2005037055 A2 | 4/2005 |
| WO | 2008074039 A1 | 6/2008 |
| WO | 2020028847 A1 | 2/2020 |

OTHER PUBLICATIONS

PCT/US2019/044966 filed Aug. 2, 2019 International Search Report and Written Opinion dated Oct. 25, 2019.
EP 198447955 filed Feb. 11, 2022 Extended European Search Report dated Jun. 30, 2022.

* cited by examiner

PROXIMAL

DISTAL

PROXIMAL

DISTAL

IMPLANTABLE PORT PLACEMENT SYSTEM INCLUDING LOW-SCARRING EXTERIOR

PRIORITY

This application is a U.S. national stage application of International Application No. PCT/US2019/044966, which claims the benefit of priority to U.S. Provisional Application No. 62/713,968, filed Aug. 2, 2018, U.S. Provisional Application No. 62/743,434, filed Oct. 9, 2018, and U.S. Provisional Application No. 62/743,419, filed Oct. 9, 2018, each of which is incorporated by reference in its entirety into this application.

BACKGROUND

Current implantable access port ("port") placement involves a multi-step process requiring a scalpel to form an incision, a Kelly clamp or similar device for blunt dissection of the subcutaneous tissues to form a tissue pocket, repeated insertion of the port to ensure a snug fit, placing the port, and lastly closing the incision. The repeated insertion of the port is often necessary to ensure the tissue pocket is sufficiently large enough to receive the port, while at the same time is not too large so as to prevent the port traveling or inverting after it has been placed.

The placement process also leaves behind scars that can be several centimeters long. Scar formation is exacerbated by tension on the skin during port placement and during wound healing. This is of particular significance for ports defining larger vertical profiles such as power injection ports, that place increased tension on the incision and surrounding tissue, exacerbating scar tissue formation. The vertical heights of existing power injection ports are influenced by two factors, the thickness of the septum, and the depth of the reservoir for accommodating the bevel of the access needle.

For power injection ports, septum thickness needs to be sufficient to prevent rupturing when contrast fluid is introduced under pressure. Further, the configuration of Huber-type, non-coring access needles with sufficient lumen diameter to provide the necessary flow rate, e.g., at least about 1 milliliter per second, results in an extended needle bevel to accommodate the lumen opening. Accordingly, the reservoir depth is also required to be sufficient to fit the entire needle bevel into the reservoir. If the needle bevel is not entirely within the reservoir, the contrast fluid can escape to the surrounding tissues, and is detrimental to the patients' health. The combined effect of these two factors demand power injection ports to have a relatively large transverse profiles. Accordingly, implanting such ports requires substantial stretching of incision site and the surrounding tissues, inducing scarring.

What is needed therefore, is a system and a method for streamlining the port placement process. The placement system, including a placement tool and a port, simultaneously forms an incision, dissect tissue, create a tissue pocket of the correct size for the port being placed, and place the port subcutaneously. This results in reduced procedure times, reduced scarring, and minimized wound management. Further, the port includes features that allow for a low overall profile, while still capable of withstanding power injection. Thus reducing tension on the tissue pocket and incision site, reducing potential scarring.

SUMMARY

Embodiments of the present invention are generally directed to an implantable access port configured to provide needle access to a vasculature of a patient for the delivery of medicaments or the like. In accordance with one embodiment, the access port is shaped and configured to minimize scarring to a patient after the port has been subcutaneously implanted.

Disclosed herein is a subcutaneous access port system, comprising of a placement tool including a proximal handle and a distal port holder, and an implantable access port releasably secured to the port holder, the port comprising of a housing including a base and a reservoir, a needle-penetrable septum covering the reservoir, and a body coupled to the housing over the needle-penetrable septum, the body comprising of a stem cover configured to engage the distal port holder, and a tunneling edge opposite of the stem cover designed to dissect tissue as the implantable access port is urged subcutaneously.

In some embodiments, the subcutaneous access port system further comprises an indicia marker, the indicia marker disposed between the base and the body. The indicia marker is radiopaque and includes one of an alphanumeric symbol and shape denoting one of a feature and an orientation of the port. The placement tool engages an outer surface of the stem cover. The placement tool engages one of an inner surface of the stem cover, an end surface of the stem cover, and a stem aperture of the housing, the stem aperture also configured for receiving a stem portion, the stem portion providing fluid communication between the reservoir and a catheter attached thereto. The stem cover includes one of a protrusion, a detent, and a socket, configured to engage the placement tool. The body further includes a skive on a side surface thereof, the skive defining a tapered footprint of the distal portion of the body. The septum defines a convex upper surface to allow a needle to access the reservoir at an acute angle relative to a skin surface of the patient. A vertical depth of the reservoir is less than a maximum length of a bevel of an access needle, accessing the port. A footprint shape of the port includes one of a circular, crescent, reniform, elongate balloon and arrow shape.

In some embodiments, the septum includes a reinforcement. The reinforcement includes one of a wire reinforcement and a matrix reinforcement. The reinforcement includes a wire mesh. The reinforcement includes a plurality of individual wire strands, and one of the individual wire strands extends through a center-point of the septum. The reinforcement includes a matrix of silicone rubber with one of a plurality of particles and a plurality of fibers disposed therein. The plurality of particles are formed of one or more of a metal, a ceramic, and a polymer, and the particles range in size from 10 nm to 1.0 mm in diameter. The plurality of fibers are formed of one or more of a metal, a ceramic, and a polymer, and the fibers range in length from 1 mm and 15 mm in diameter.

Also disclosed herein is a system for placing an implantable port, comprising of a port; and a placement tool, comprising of an elongate body including a handle, a port holder disposed at a distal end of the elongate body and configured to releasably secure the port thereto, the port holder including a base, a curved panel, and a tunneling edge, and an actuator configured for selectively releasing the port.

In some embodiments, the base defines a perimeter, the shape of the perimeter matching the shape of a footprint of the port. The base and the curved panel define a recess, the recess configured to receive a distal portion of the port. The tunneling edge is sharpened and configured to dissect tissue when the placement tool is urged subcutaneously. The curved panel is formed of a first panel arm and a second panel arm, each of the first and second panel arms being hingedly coupled to the port holder. The actuator operably connects to the first and second panel arms, the actuator selectively moving the first and second panel arms between a closed position that retains the port, and an open position that releases the port.

Also disclosed herein is a port placement tool for placing an access port subcutaneously, comprising of a first elongate arm extending from a proximal end to a distal end, including a first gripping feature disposed at a proximal end and a first port holder disposed a distal end, a second elongate arm extending from a proximal end to a distal end, including a second gripping feature disposed at a proximal end and a second port holder disposed a distal end, and the first arm and the second arm hingedly connected at a mid-portion, one of the first port holder and the second port holder including a blade extending from a distal portion thereof.

In some embodiments, the first and second port holders include curved loops, shaped to receive a portion of an implantable access port. The first port holder includes a first blade and the second port holder includes a second blade, each of the first and second blades engage at a lateral mid-point of the tool.

Also disclosed herein is a method of subcutaneously placing an implantable access port, comprising of providing a port implantation system including a port and a placement tool, the port including a tunneling portion and a stem cover, the tunneling portion terminating in a tunneling edge, the stem cover extending over a stem portion of the port, and the placement tool engaging the stem cover to releasably secure the port to a distal end of the placement tool, inserting the tunneling edge through an incision on a skin surface of a patient, creating a tissue pocket using the tunneling portion of the port by urging the port subcutaneously to dissect subcutaneous tissue, releasing the port from the placement tool, and withdrawing the placement tool from the body of the patient. In some embodiments, the tunneling edge is sharpened. The incision is formed by one of a scalpel and a sharpened tunneling edge.

Also disclosed herein is a method of placing an access port subcutaneously, comprising of providing a port implantation system, the system including a placement tool and a port, the placement tool including a port holder configured for receiving the port, the port holder including a curved panel defining a recess and a tunneling edge, releasably securing the port to the port holder, creating an incision using the tunneling edge of the placement tool by inserting the port holder through a skin surface of a patient, creating a tissue pocket using the curved panel of the placement tool by urging the port holder subcutaneously to dissect subcutaneous tissue, releasing the port from the placement tool, and withdrawing the placement tool from the body of the patient. In some embodiments, the tunneling edge is sharpened.

DRAWINGS

Figure 1B:
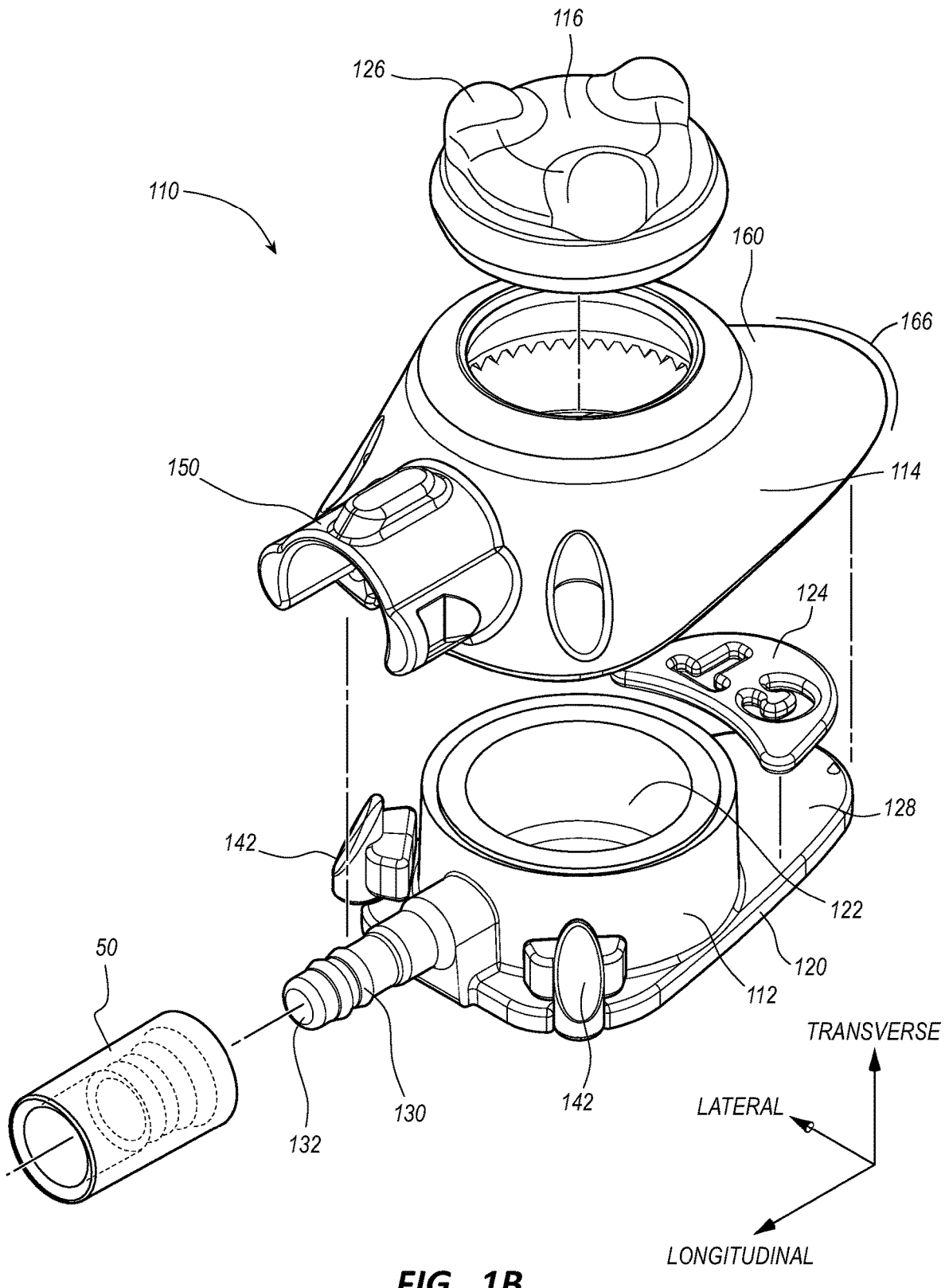
Figures 1C, 1D:
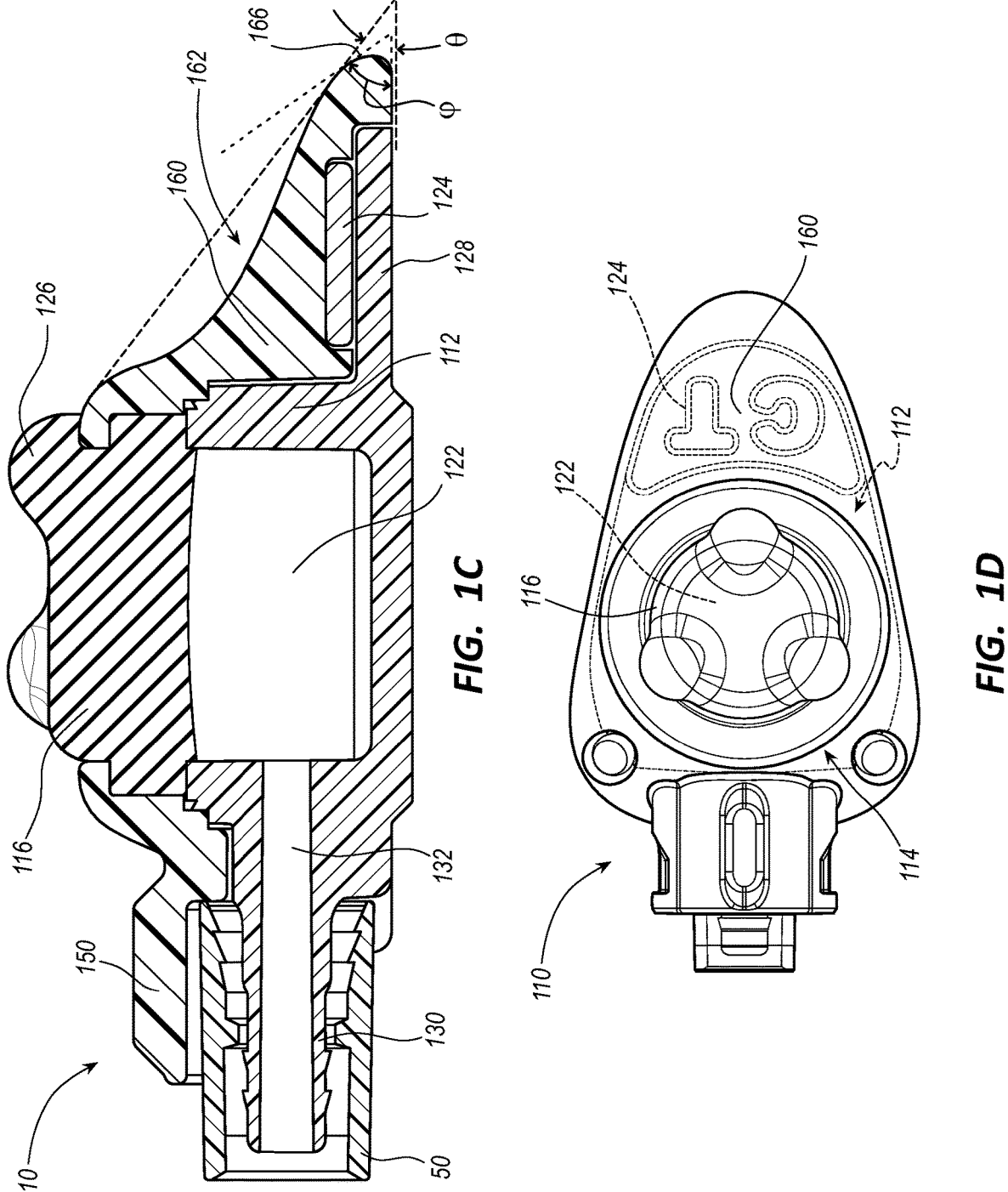
Figure 2A:
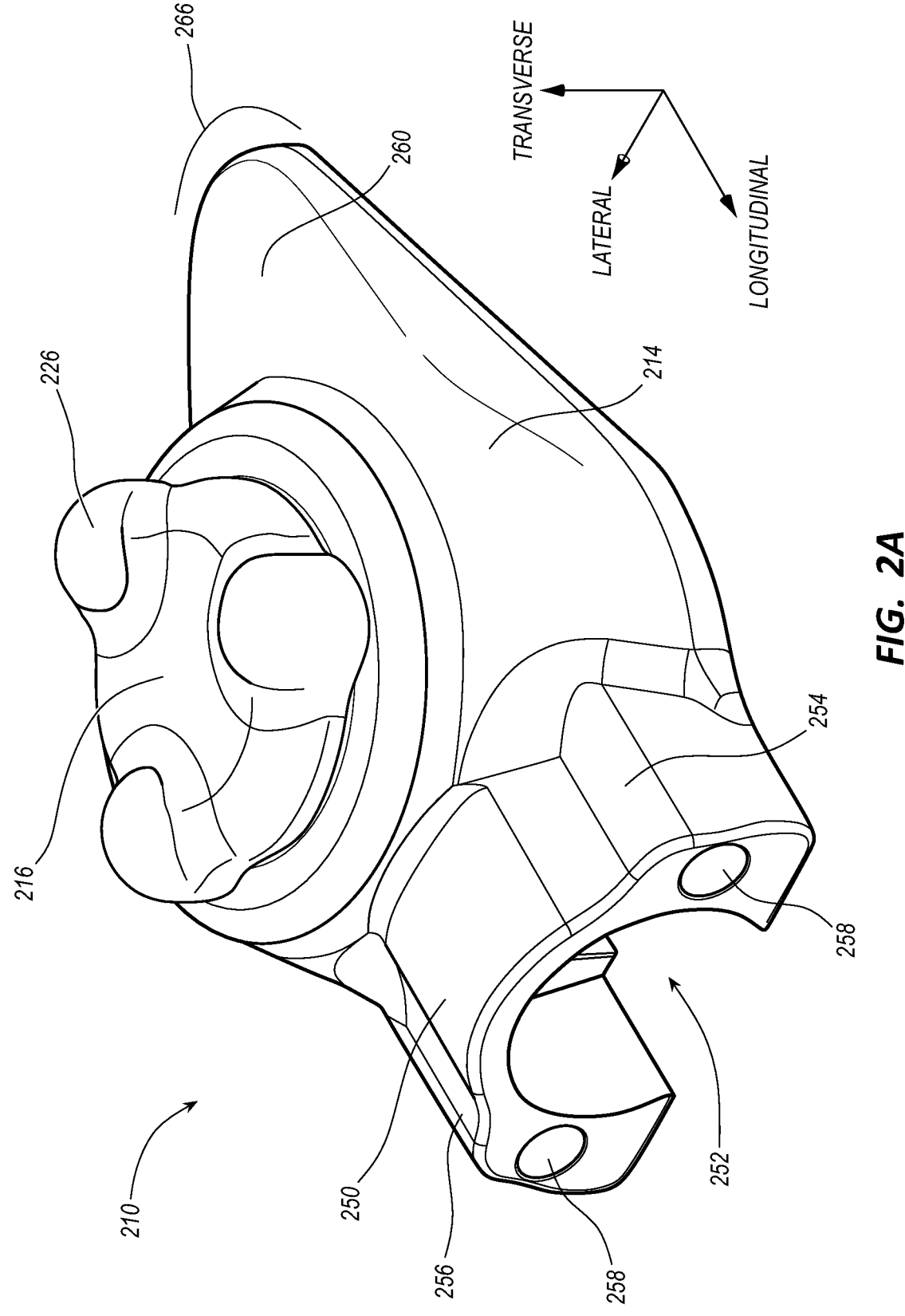
Figure 2B:
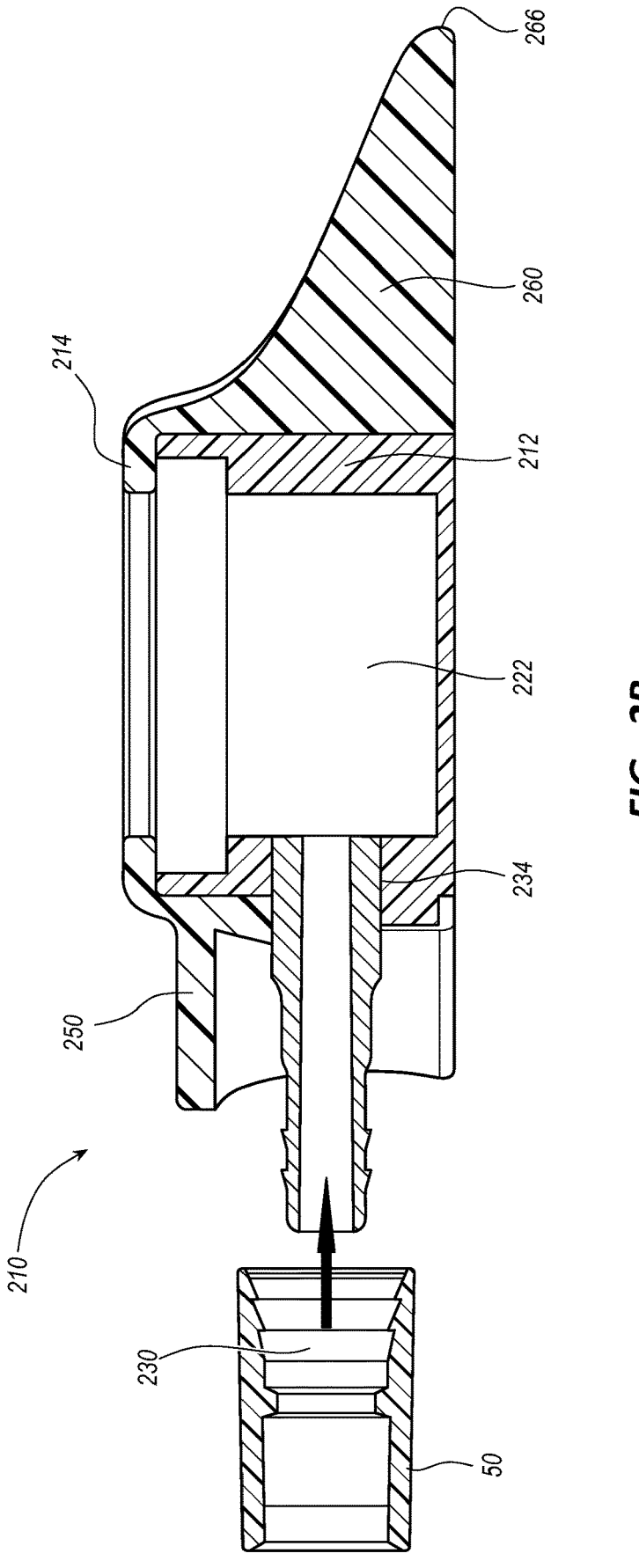
Figures 2C, 2D, 2E, 2F:
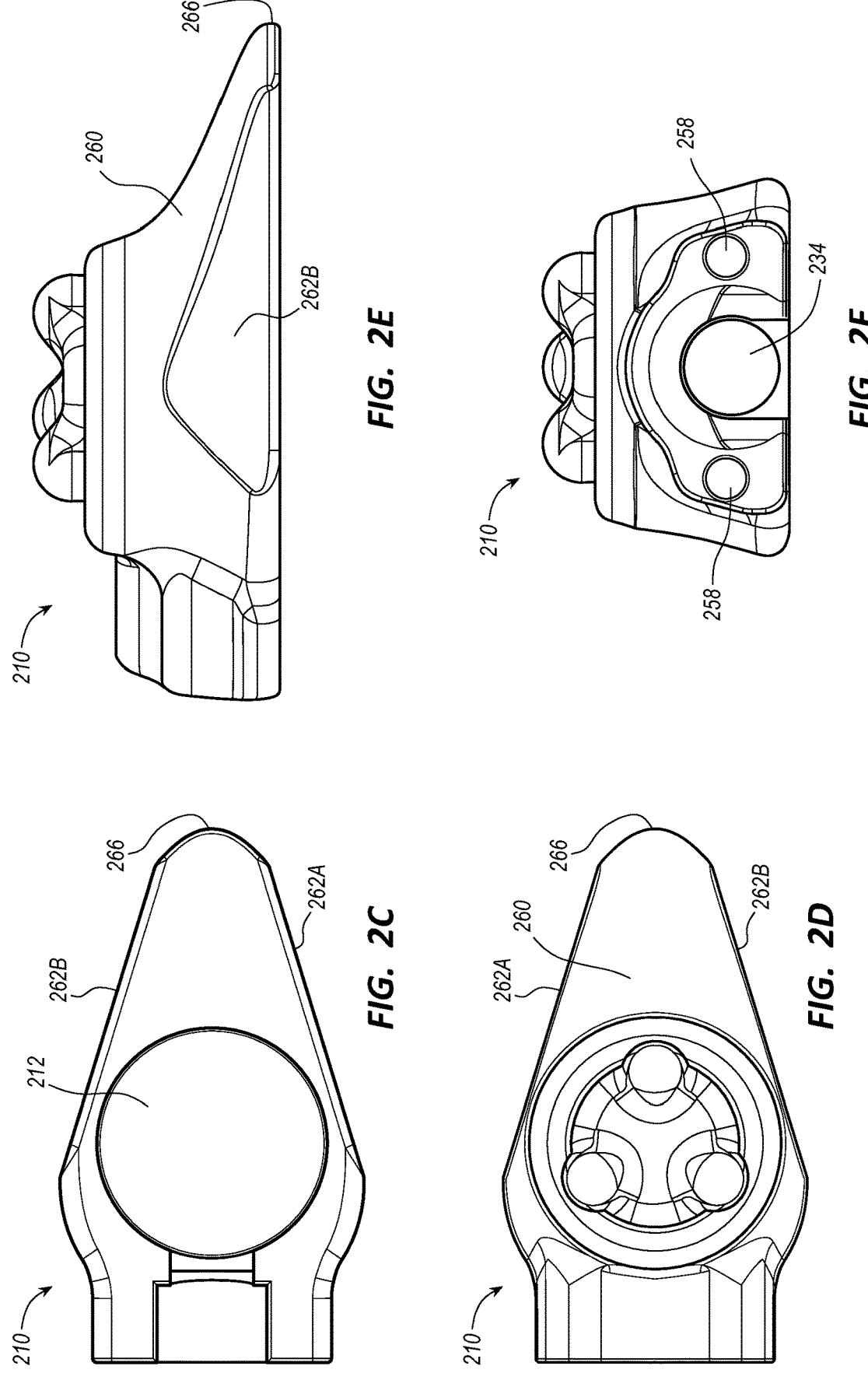
Figures 2G, 2H:
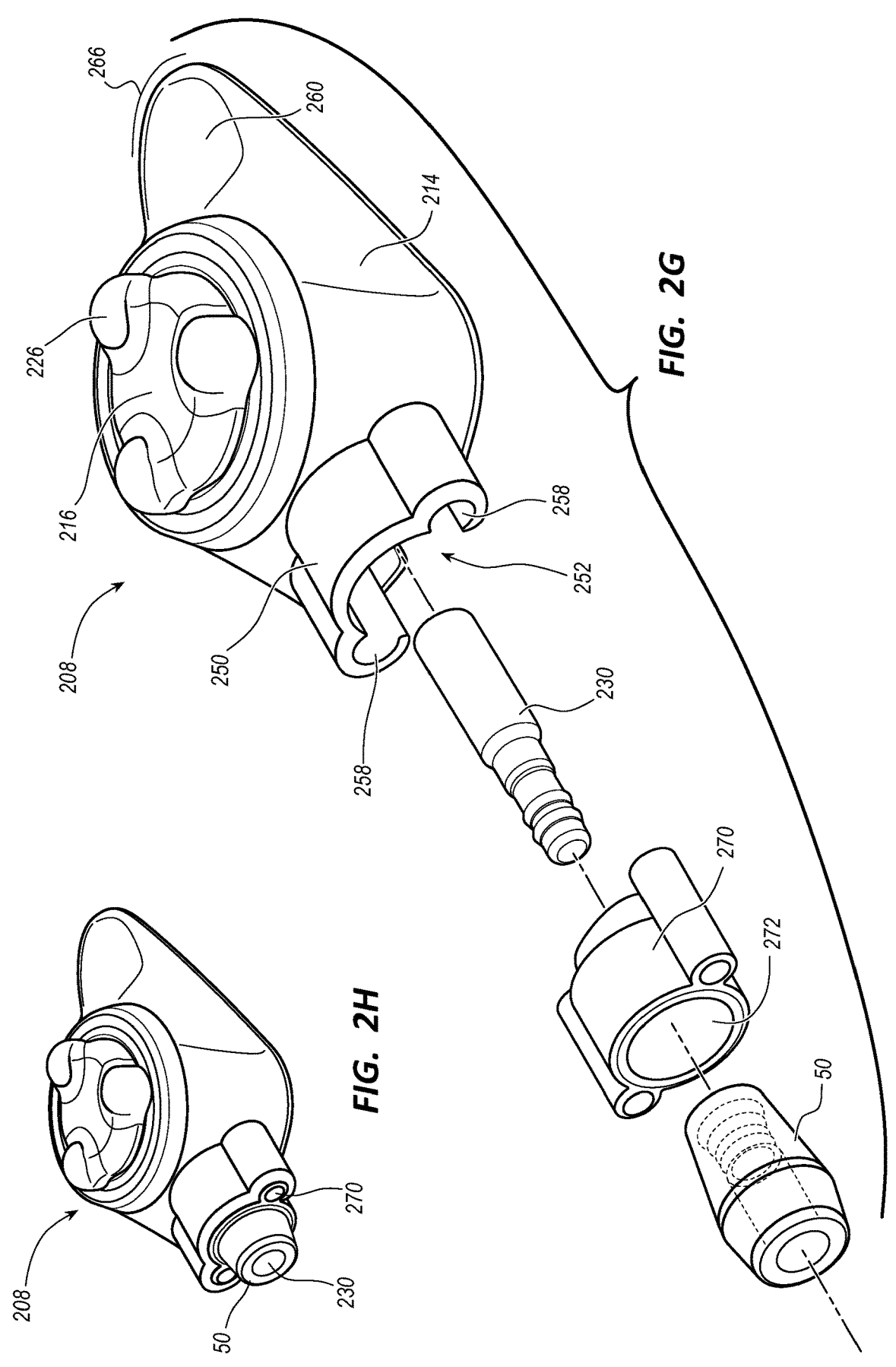
Figure 3A:
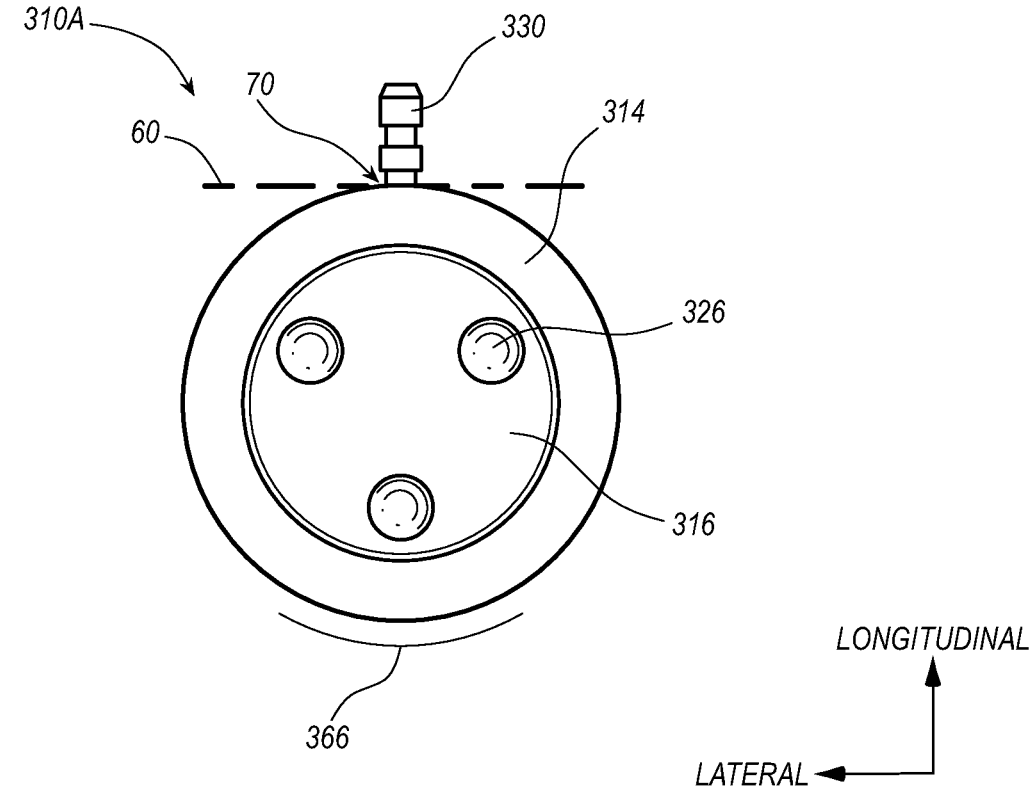
Figure 3B:
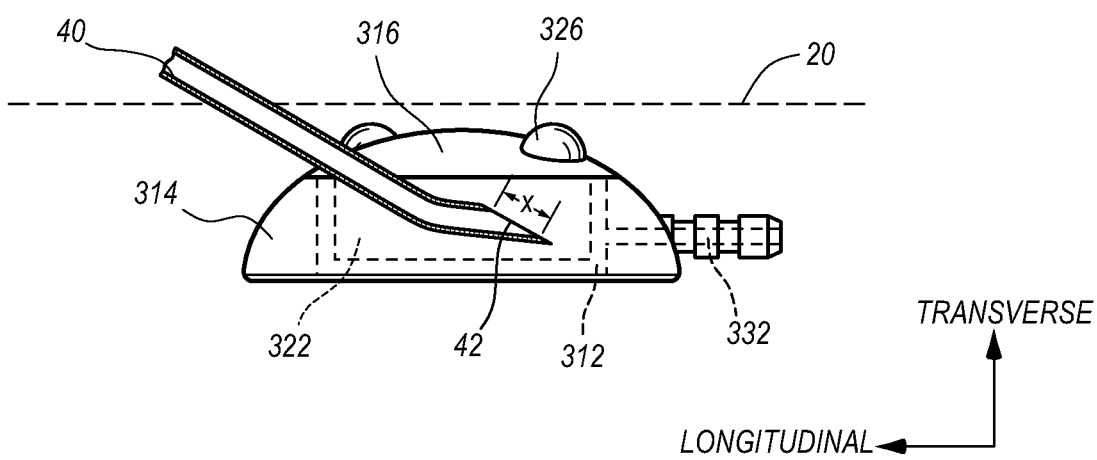
Figure 3C:
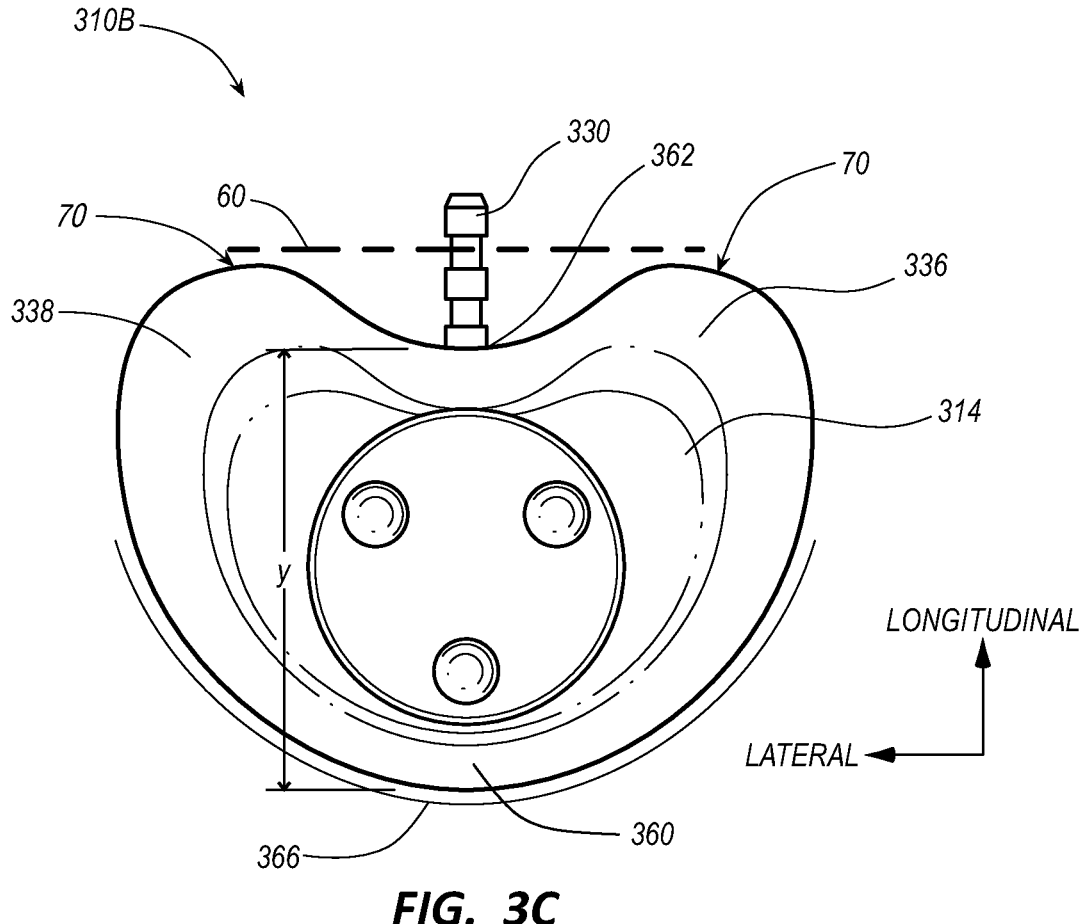
Figure 3D:
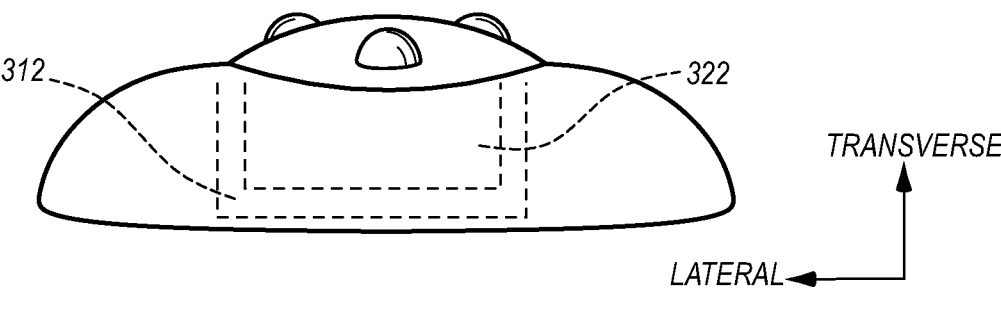
Figure 3E:
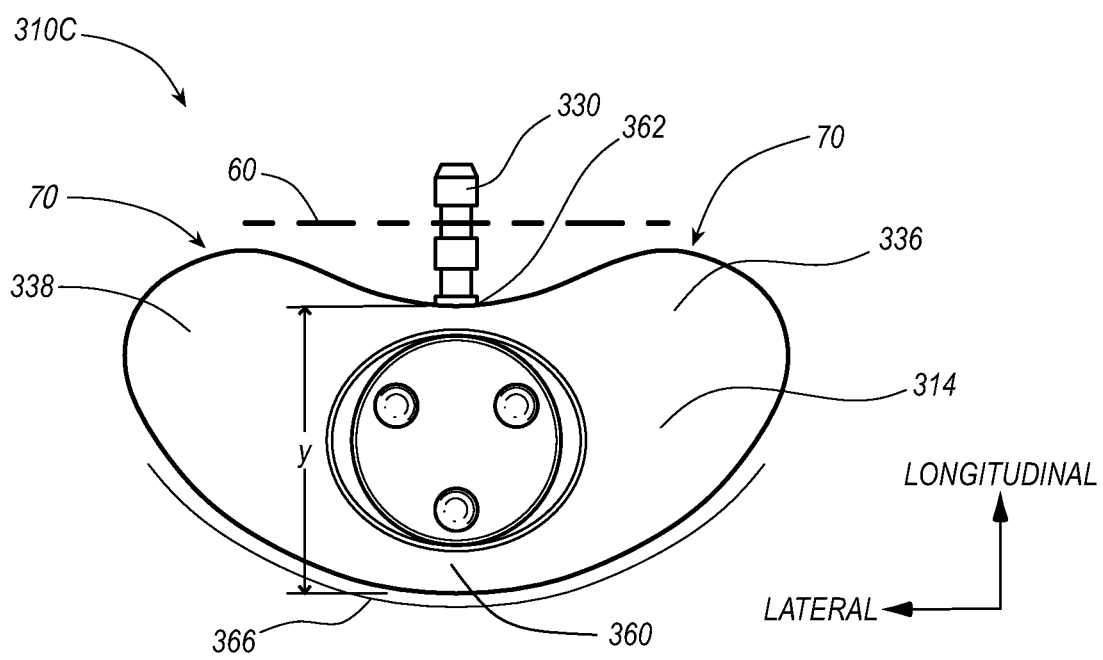
Figure 3F:
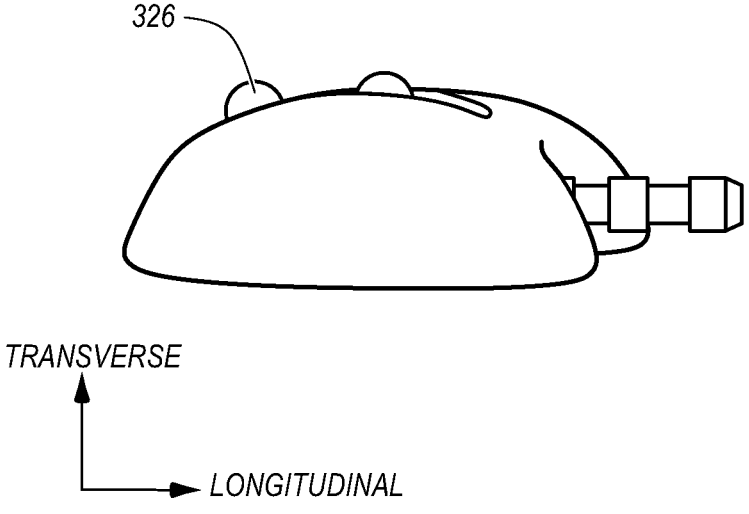
Figure 3G:
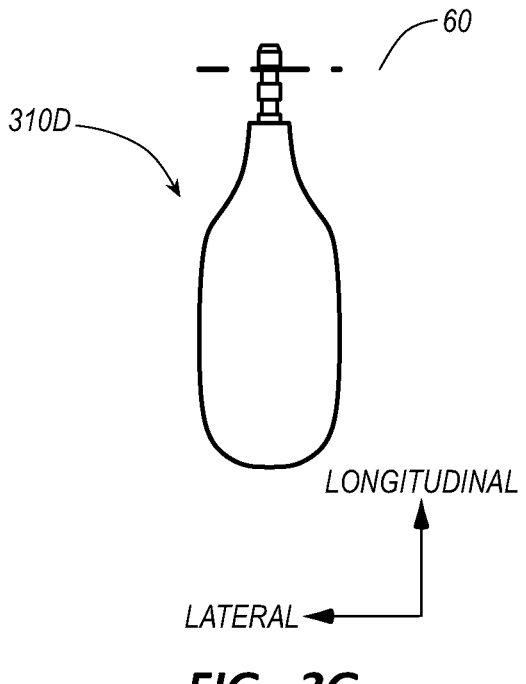
Figure 3H:
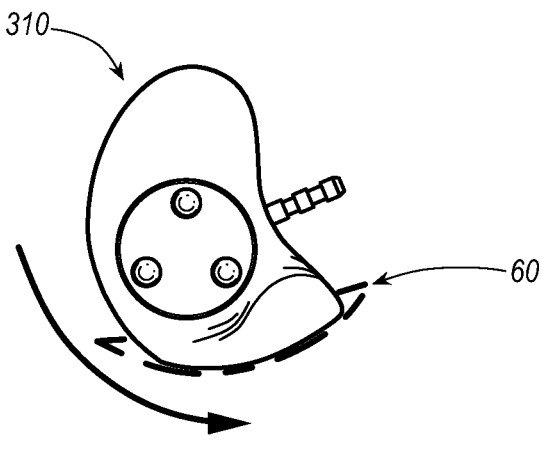
Figure 5A:
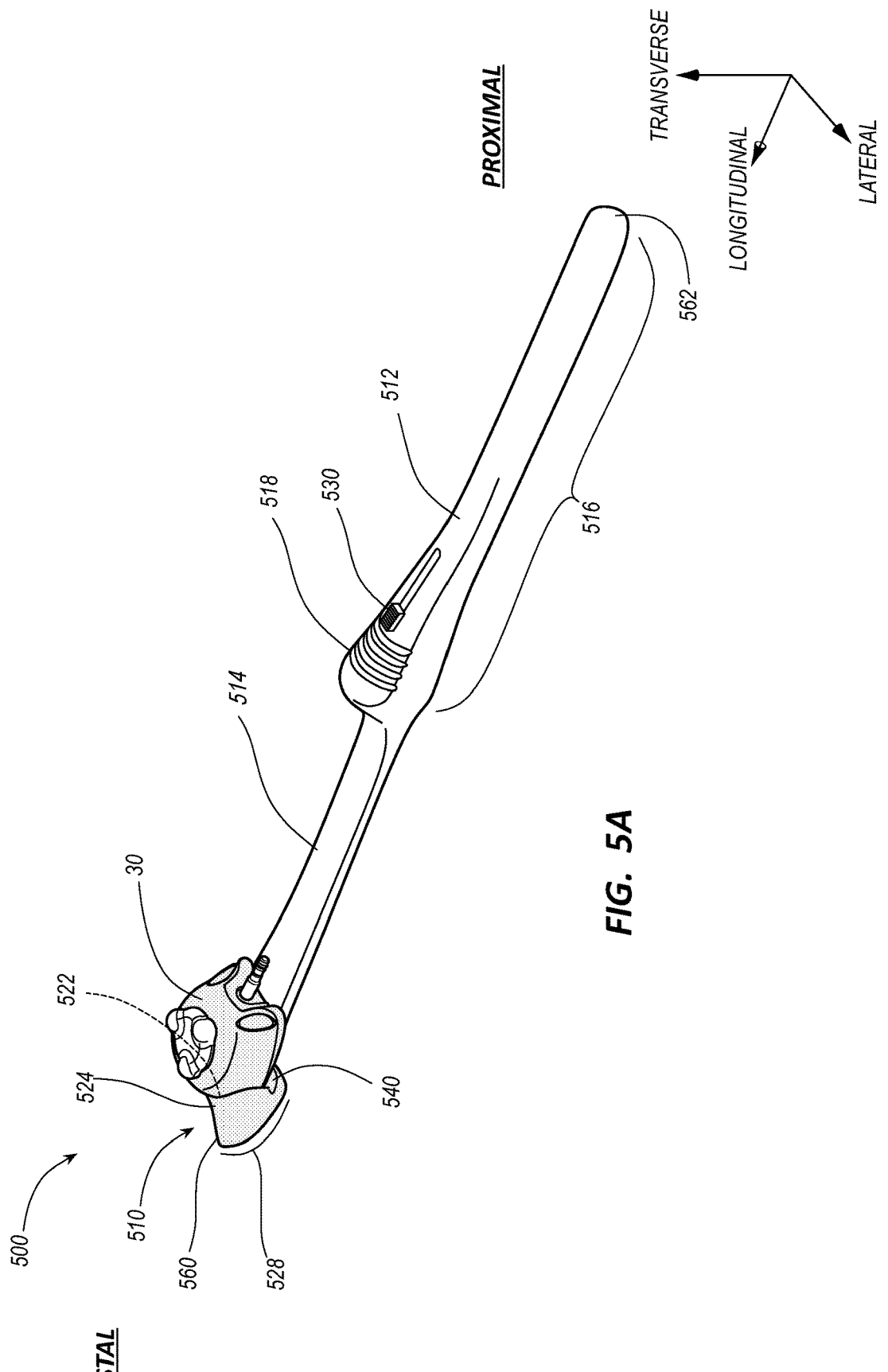
Figures 5B, 5C, 5D:
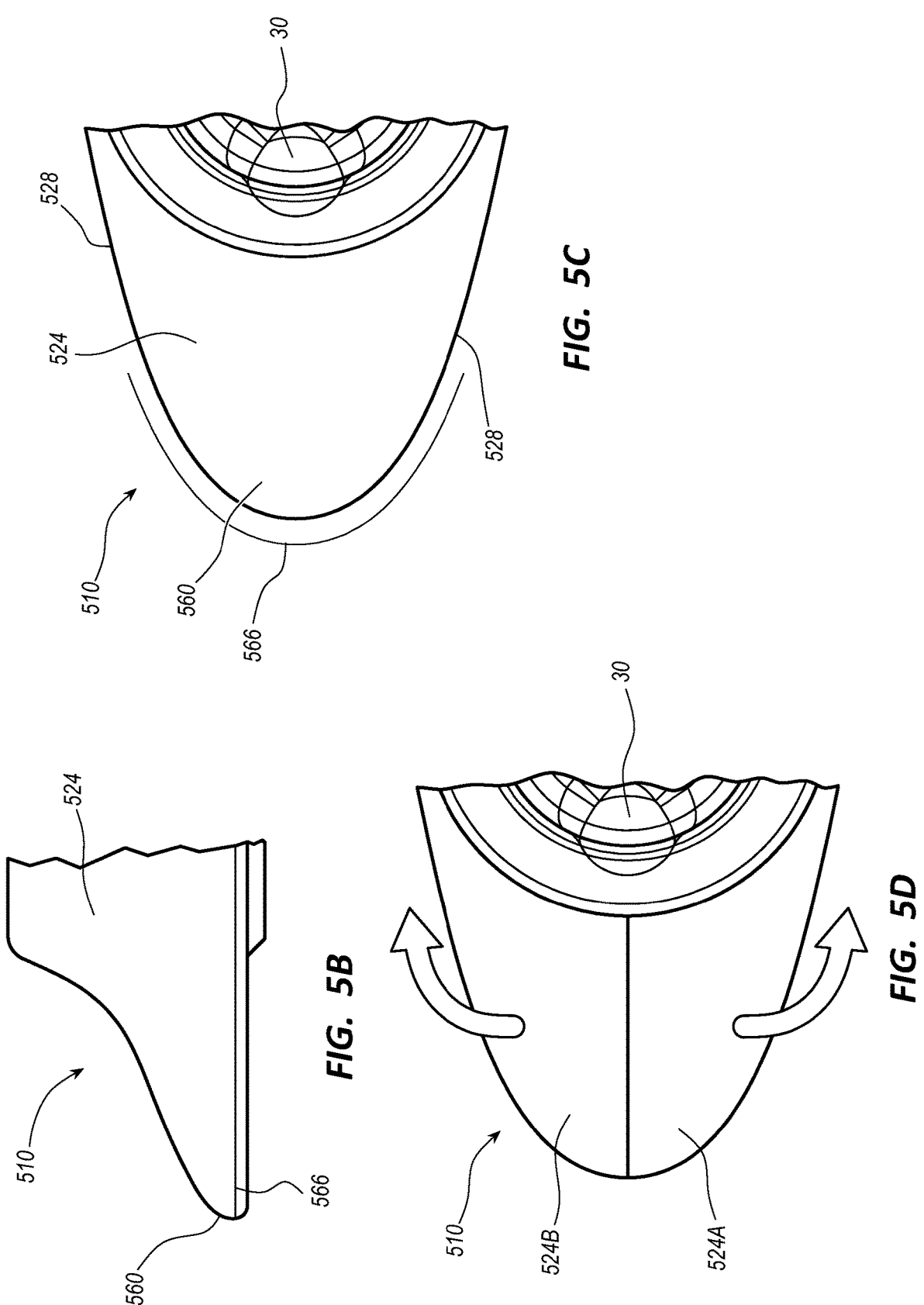
Figure 6:
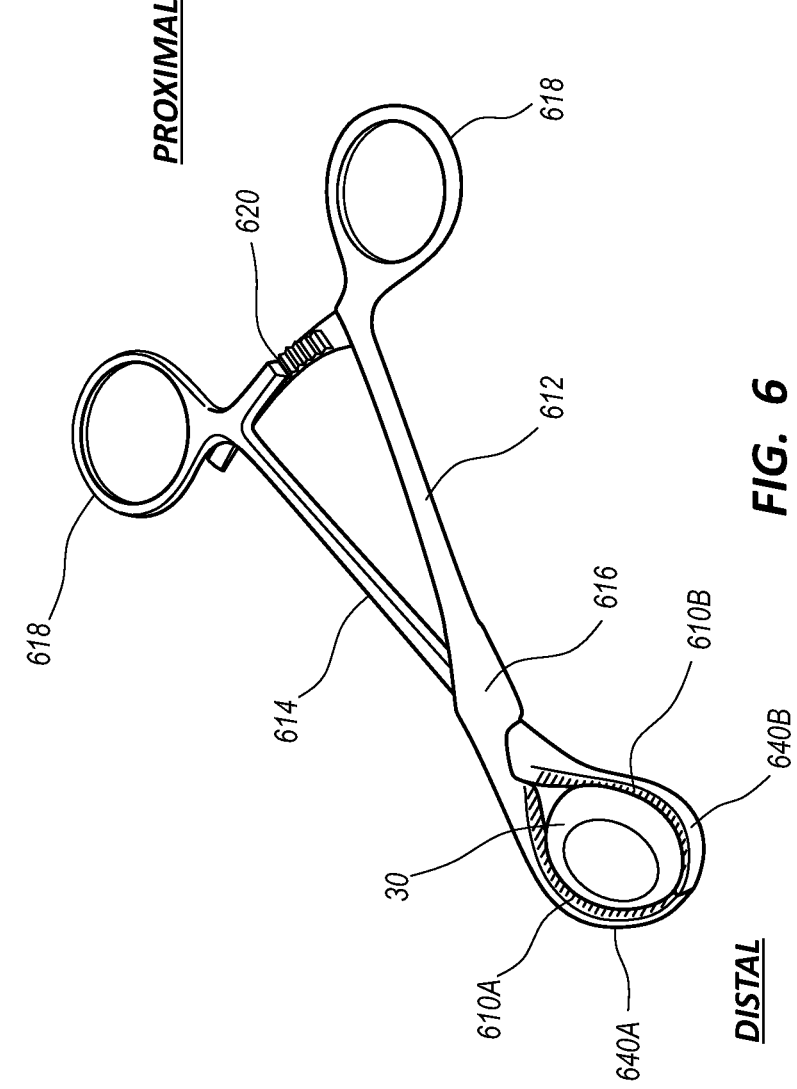
Figure 5E:
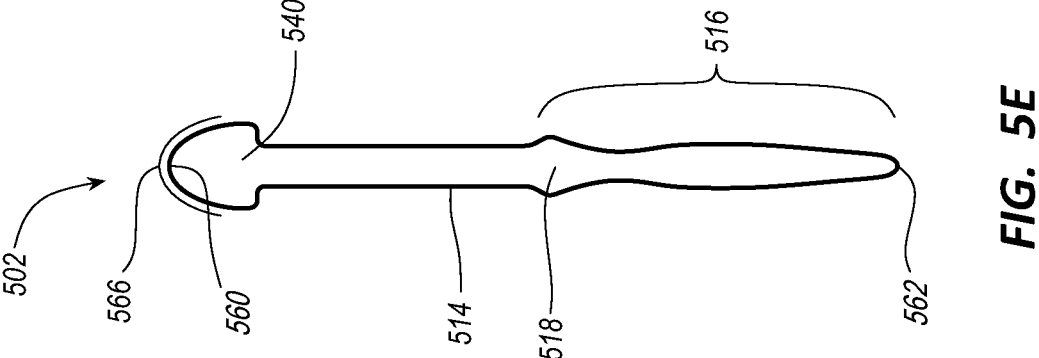
Figure 7:
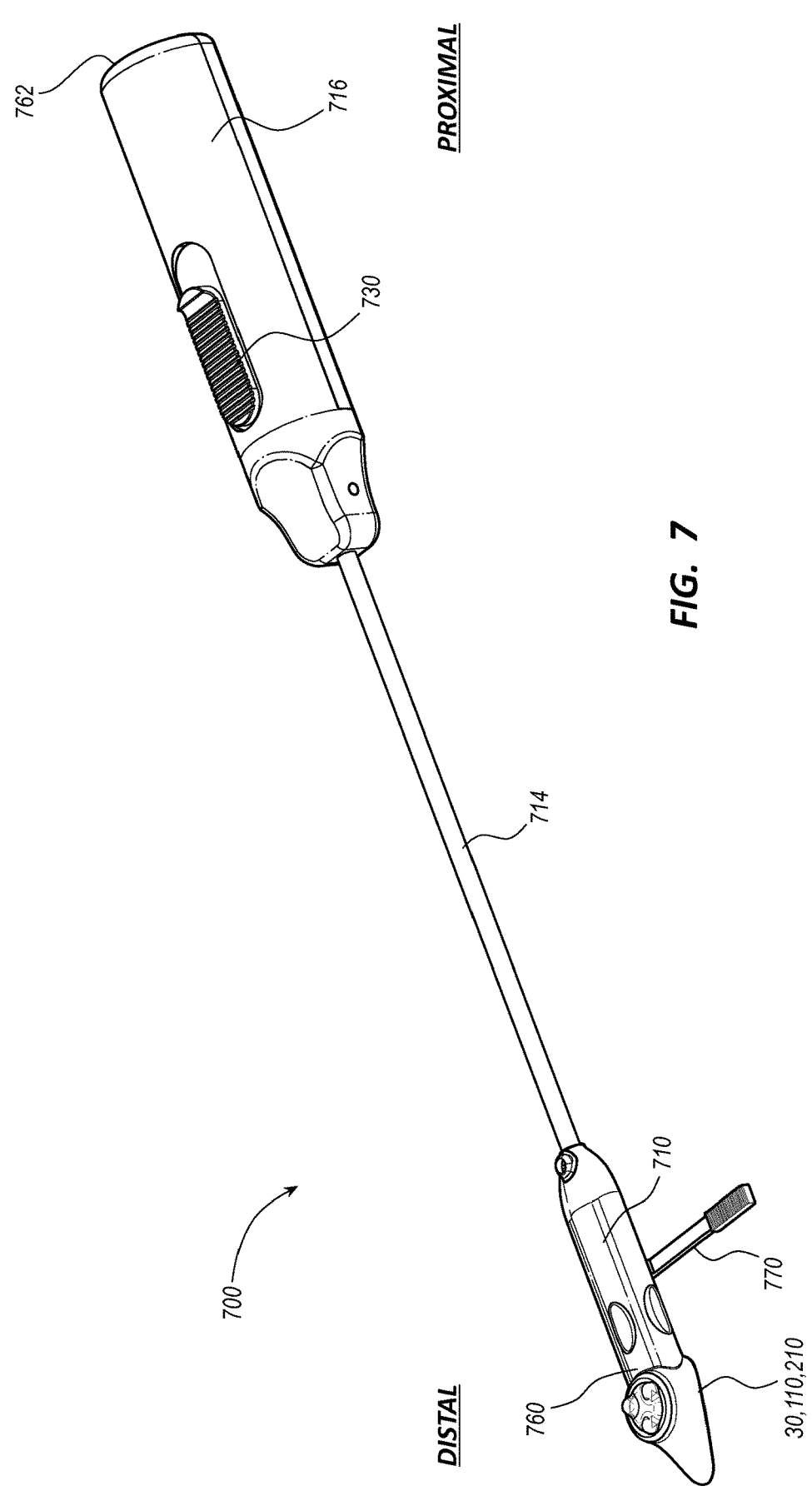

A more particular description of the present disclosure will be rendered by reference to specific embodiments thereof that are illustrated in the appended drawings. It is appreciated that these drawings depict only typical embodiments of the invention and are therefore not to be considered limiting of its scope. Features from a given embodiment can be incorporated into other embodiments without departing from the spirit of the invention. Example embodiments of the invention will be described and explained with additional specificity and detail through the use of the accompanying drawings in which:

FIG. 1A provides a perspective view of an implantable access port ("port") in accordance with embodiments disclosed herein;

FIG. 1B provides an exploded view of a port in accordance with embodiments disclosed herein;

FIG. 1C provides a cross-sectional side view of a port in accordance with embodiments disclosed herein;

FIG. 1D provides a plan view of a port with the port body, port housing, a septum, indicia, and a catheter lock, in accordance with embodiments disclosed herein;

FIG. 2A provides a perspective view of a port in accordance with embodiments disclosed herein;

FIG. 2B provides a cross-sectional side view of a port in accordance with embodiments disclosed herein;

FIG. 2C provides an underside view of a port in accordance with embodiments disclosed herein;

FIG. 2D provides a plan view of a port in accordance with embodiments disclosed herein;

FIG. 2E provides a side view of a port in accordance with embodiments disclosed herein;

FIG. 2F provides a proximal side view of a port in accordance with embodiments disclosed herein;

FIG. 2G provides an exploded perspective view of a port in accordance with embodiments disclosed herein;

FIG. 2H provides a perspective view of a port in accordance with embodiments disclosed herein;

FIG. 3A provides a plan view of a port in accordance with embodiments disclosed herein;

FIG. 3B provides a side view of a port in accordance with embodiments disclosed herein;

FIG. 3C provides a plan view of a port in accordance with embodiments disclosed herein;

FIG. 3D provides a tunneling end view of a port in accordance with embodiments disclosed herein;

FIG. 3E provides a plan view of a port in accordance with embodiments disclosed herein;

FIG. 3F provides a side view of a port in accordance with embodiments disclosed herein;

FIG. 3G provides a plan view of a port in accordance with embodiments disclosed herein;

FIG. 3H provides a perspective view of a port being inserted subcutaneously in accordance with embodiments disclosed herein;

FIGS. 4A-4D provide perspective views of a septum in accordance with embodiments disclosed herein;

FIG. 5A provides a perspective view of an implantable access port placement tool ("placement tool,") including an access port, in accordance with embodiments disclosed herein;

FIGS. 5B-5D provide various views of embodiments of a distal portion of the placement tool of FIG. 5A in accordance with embodiments disclosed herein;

FIG. 5E provides a plan view of a placement tool in accordance with embodiments disclosed herein;

FIG. 6 provides a perspective view of a placement tool, including an access port, in accordance with embodiments disclosed herein; and FIG. 7 provides a perspective view of a placement tool, including an access port, in accordance with embodiments disclosed herein.

DESCRIPTION

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "front," "back," "top," "bottom," "forward," "reverse," "clockwise," "counter clockwise," "up," "down," or other similar terms such as "upper," "lower," "aft," "fore," "vertical," "horizontal," "proximal," "distal," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a medical device disclosed herein includes a portion of the medical device intended to be near a clinician when the medical device is used on a patient. Likewise, a "proximal length" of, for example, the device includes a length of the device intended to be near the clinician when the device is used on the patient. A "proximal end" of, for example, the device includes an end of the device intended to be near the clinician when the device is used on the patient. The proximal portion, the proximal end portion, or the proximal length of the device can include the proximal end of the device; however, the proximal portion, the proximal end portion, or the proximal length of the device need not include the proximal end of the catheter. That is, unless context suggests otherwise, the proximal portion, the proximal end portion, or the proximal length of the device is not a terminal portion or terminal length of the device.

With respect to "distal," a "distal portion" or a "distal end portion" of, for example, a medical device disclosed herein includes a portion of the medical device intended to be near or in a patient when the device is used on the patient. Likewise, a "distal length" of, for example, the device includes a length of the device intended to be near or in the patient when the device is used on the patient. A "distal end" of, for example, the device includes an end of the device intended to be near or in the patient when the device is used on the patient. The distal portion, the distal end portion, or the distal length of the device can include the distal end of the device; however, the distal portion, the distal end portion, or the distal length of the device need not include the distal end of the device. That is, unless context suggests otherwise, the distal portion, the distal end portion, or the distal length of the device is not a terminal portion or terminal length of the device.

As used herein, a "footprint" is a two-dimensional area substantially defined by a perimeter of an object when viewed from a plan view perspective. As used herein, the term "sharpened" is defined as a reduction in a radius of curvature between two facets, from that of a substantially rounded edge to that of a relatively more angular edge. Unless defined otherwise, all technical and scientific terms used herein have the same meaning as commonly understood by those of ordinary skill in the art.

Embodiments of the present invention are generally directed to implantable access ports and placement tools. The ports are configured to provide needle access to a vasculature of a patient for the delivery of medicaments or the like. In accordance with embodiments disclosed herein, the access port is shaped and configured to define a low profile and minimize scarring to a patient after the port has been subcutaneously implanted. Further implantation tools facilitate the incision, dissection, sizing and placing of the port, simplifying the process for inserting the access device within the patient.

Implantable Access Port

FIGS. 1A-D show various details of an implantable access port ("port") 110 according to an exemplary embodiment. The port 110 includes a port housing ("housing") 112, a port body ("body") 114, and a needle penetrable septum ("septum") 116. The port 110 includes a stem side, from which a stem portion 130 extends, and a tunneling side, opposite the stem side and used to define a tissue pocket, as described in more detail herein. The housing 112 includes a housing base 120 extending substantially horizontally from a stem side, to a tunneling side. A reservoir 122 is disposed on an upper surface of the base 120, and a stem portion ("stem") 130 extends horizontally from a stem side of the housing 112. The housing base 120 further includes an extended tunneling portion 128 for supporting indicia 124 and a tunneling portion 160 of the body 114.

The stem 130 can be coupled with a catheter, catheter locking device 50, or combinations thereof, or similar endovascular device. As used herein, the "catheter 50" includes a portion of a catheter that engages the stem and any associated locking mechanisms, collars, barb features, combinations thereof, or the like for securing the catheter to the stem 130. The stem 130 defines a lumen 132 extending from the reservoir 122 and provides fluid communication between the reservoir 122 and the catheter 50.

As shown in FIG. 1C, the septum 116 is disposed over the reservoir 122 and secured in place by the port body 114. In an embodiment, the septum 116 includes palpation features 126, such as bumps. Examples of palpation features can be found in U.S. Pat. No. 8,177,762, filed Dec. 28, 2005; U.S. Pat. No. 8,608,713, filed May 14, 2012; U.S. 2014/0100534, filed Dec. 12, 2013; U.S. Pat. No. 9,579,496, filed Nov. 7, 2008; U.S. Pat. No. 10,086,186, filed Feb. 24, 2017; U.S. 2019/0060628, Sep. 24, 2018; U.S. Pat. No. 8,932,271, filed Nov. 13, 2009; U.S. Pat. No. 10,052,471 filed Dec. 31, 2014; and U.S. 2018/0353743, filed Aug. 20, 2018, each of which are incorporated by reference in their entirety into this application. Once the port 110 is subcutaneously implanted, the palpation features 126 allow a clinician to locate the port 100 and more specifically the septum 116 in order to access the port 110. The palpation features 126 can vary in number and position and can indicate to a clinician the location and orientation of the port 110.

FIG. 1D shows a plan view perspective of the port 110. The port 110, including the tunneling portions 128, 160 provide a substantially triangular, arrow-like, shaped footprint. The reservoir 122 as shown defines a substantially circular footprint, although it will be appreciated that other shaped footprints are contemplated. The housing 112 can be formed of a substantially rigid material, such as polymers, plastics, titanium, stainless steel, or similar suitable materials.

In an embodiment, a tunneling edge 166 of the port body 114, substantially opposite the stem side defines a sharp edge to facilitate placement of the port 110 within the patient. In an embodiment, the tunneling edge 166 facilitates separation of the tissue and forms a tissue pocket when the port 110 is urged subcutaneously into the patient. As shown in FIG. 1C, a side view of the tunneling edge 166 provides an angle φ. The angle of the tunneling edge p can be between 3° and 89°. In an embodiment, the tunneling edge 166 defines a rounded edge for blunt dissection of the tissues.

In an embodiment, the port body 114 is formed of a relatively pliable material, such as silicone rubber or similar suitable material, and can be overmolded onto the housing 112. In another embodiment, the body 114 is formed of a more rigid material, such as plastic, polymer, stainless steel, titanium, or similar material to that of the housing 112, and can be snap-fitted or press-fitted onto the port housing 112. In another embodiment, the body 114 is formed of a combination of pliable and rigid materials. For example, some portions of the body 114 can be formed of a pliable material while other portions, such as tunneling portion 160, tunneling edge 166, or combinations thereof include a rigid material. The pliable material can reduced stress points along a port body, and therefore reduce scarring, while the rigid material can provide a tunneling edge to separate the tissue as the port 110 is urged into the patient. In an embodiment, the tunneling edge can be sharpened sufficiently so that it is capable of nicking the skin to form an incision. In an embodiment the tunneling edge 166 includes a blade for nicking the skin to form an incision. In an embodiment, the blade can be selectively retractable.

In an embodiment, the outer profile of the port body 114 defines a smooth, unobtrusive shape that reduces tissue stress points on an exterior of the port 110. The port body profile minimizes tension on the subcutaneous tissue during placement, this in turn minimizes the formation of scar tissue. As shown in FIG. 1C, in an embodiment, a tunneling portion 160 of the body 114 extends from a tunneling side of the reservoir 122, away from the stem side to define an extended-sigmoid, sloped profile, when viewed from a side view perspective. The angle θ of the tunneling portion 160 can be between 3° and 89°. In an embodiment, the angle θ can be less than the angle φ of the tunneling edge 166. In an embodiment, the angle θ can be greater than the angle φ of the tunneling edge 166. In an embodiment, the angle θ can be substantially the same as the angle φ of the tunneling edge 166. The sigmoid profile of the tunneling portion 160, provides a hollow 162 between a tunneling edge 166 and the reservoir 122. The hollow 162 provides a frictionless air gap between the surface of the tunneling portion 160 and the tissues that are being separated, which facilitates dissection of tissue and formation of a tissue pocket as the port is urged subcutaneously. In an embodiment, the side elevation profile of the tunneling portion 160 can include other shapes such as straight, convex, concave, or combinations thereof.

As shown in FIGS. 1B-1C, the port 110 further includes indicia 124. The indicia 124 can include a radiopaque marker, formed of titanium or similar suitable radiopaque material, so as to be visible under fluoroscope, ultrasound, or similar imaging medium, once the port 100 is subcutaneously implanted. The indicia 124 can include symbols engraved therein to indicate an orientation, feature, or combinations thereof about the port. For example, the indicia 124 can have the letters "CT" engraved therein, together with being formed as a half-moon shape to indicate to a clinician the orientation of the port 110 and the suitability of the port for power injection.

The port 110 can further include one or more suture holes 140 extending through the port 110 to allow the port 110 to be secured to surrounding tissue once subcutaneously implanted. The suture holes 140 can further include suture plugs 142 disposed therein to prevent tissue ingrowth. The suture plugs 142 can be formed of silicone rubber or similar suitable needle penetrable material. As shown the suture holes are disposed at a stem side of the port 110 and oriented vertically. However, it will be appreciated that other numbers, combinations, positions, and orientations of suture holes 140 are contemplated.

In an embodiment, the port body 114 includes a stem cover 150, extending from the port body 114 and surrounds a top and side portions of the stem 130. The cover 150 can define a cylindrical shape with a substantially circular cross-section. The cover 150 further includes an opening 152 on a lower side. The opening 152 facilitates assembly of the port 110, allowing the body 114 to be urged downwards over the housing 112 and the stem 130. The cover 150 can further include one or more protrusions 154, detents 156, or combinations thereof that are configured to engage a distal end of a placement tool, for example insertion tool 700 shown in FIG. 7. In an embodiment the cover 150 is configured to substantially surround both the stem 130 and a portion of the catheter 50 that engages the stem 130. A distal portion of the placement tool 700 can then engage an outer surface of the cover 150 to manipulate both the port 110 and the catheter 50 attached thereto.

FIGS. 2A-2H, show various features of an embodiment of a port 210. Similar to embodiments described herein, the port 210 includes a port housing 212, a port body 214 including an extended tunneling portion 260 and a tunneling edge 266 that can be sharpened to facilitate implantation, and a needle penetrable septum 216, including palpation features 226. The housing 212 defines a reservoir 222 that is bounded by the needle-penetrable septum 216, and includes a stem aperture 234. The stem aperture 234 is configured for receiving a port stem 230. The port stem 230 is formed as a separate structure from the housing 212 and is configured to engage the stem aperture 234 to provide fluid communication between the reservoir 222 and a catheter 50.

In an embodiment, the port body 214 includes a stem cover 250, extending from a stem side of the port body 214. The stem cover 250 can define a cylindrical shaped recess with a substantially circular cross-section. The stem cover 250 further includes an opening 252 on a lower side. The stem cover 250 can further include one or more protrusions 254, detents 256, sockets 258, or combinations thereof that are configured to engage a distal end of a placement tool, for example placement tool 700.

In an embodiment, the distal end of the placement tool 700 engages an inner surface of the stem cover 250, an end surface of the stem cover 250, the stem aperture 234, or combinations thereof to secure the port 210 to a distal end of the placement tool 700. The placement tool can then be used to manipulate the port 210 into position within the body of the patient. Once the port 210 is in position, the tool disengages the port 210 and the clinician can optionally use the placement tool to attach the stem 230 and catheter 50. The stem 230 can be urged distally to engage the stem aperture 234. The catheter 50 can then engage the stem 230 to provide fluid communication between the reservoir 222 and the vasculature of the patient. In an embodiment, the stem 230 and catheter 50 can be attached simultaneously.

FIGS. 2C-F show various views of the port 210. As shown in FIG. 2E, in an embodiment, a tunneling portion 260 of the body 214 extends away from the stem cover 250 to define an extended sigmoid slope shape, when viewed from a side profile. The tunneling portion 260 facilitates dissection of tissue by the port 210 to form a tissue pocket, as the port is urged subcutaneously. As shown in FIGS. 2C-2D, port body 214 further includes one or more skives 262A, 262B extending along a side portion of the body 214 and angled to define a tapered, substantially triangular-shaped footprint to the port 210 when viewed from a plan view. The skives 262 further define a streamlined overall profile to the port 210 and, together with the tunneling edge 266 and profile of the tunneling portion 260, further allows the port 210 to be urged through the tissue to define a tissue pocket while minimizing potential scarring.

FIG. 2G shows an embodiment of a port 208. Similar to port 210, port 208 includes a port housing 212, a port body 214 including an extended tunneling portion 260 and a sharpened tunneling edge 266 to facilitate implantation, and a needle penetrable septum 216, including palpation features 226. The port 208 further includes a stem cover 250 extending from a stem side of the port body 214. The stem cover 250 can define a cylindrical shaped recess with a substantially circular cross-section. The stem cover 250 further includes an opening 252 on a lower side as well as one or more protrusions 254, detents 256, sockets 258, or combinations thereof that are configured to engage a distal end of a placement tool, for example placement tool 700. In an embodiment, socket 258 includes an opening on an inner surface, communicating with the cylindrical recess defined by the stem cover 250. The stem portion 230 can be formed as a separate structure from the port housing 212 and engages a stem aperture 234.

In an embodiment, an ingrowth guard 270 can be disposed within the recess defined by the stem cover 250, sockets 258, or combinations thereof. The ingrowth guard 270 further includes a recess 272 for receiving a stem 230 and a portion of a catheter and/or catheter lock 50 connected to the stem 230. As shown in FIGS. 2H, the ingrowth guard substantially fills the void created between an inner surface of the stem cover and an outer surface of the catheter 50 when coupled to the port.

Implanted subcutaneous access ports are expected to have a certain amount of ingrowth around, for example, the port, stem, etc. The amount of tissue ingrowth can increase with geometry such as holes, and indentations that provide recesses for the tissue to grow into. Advantageously, once the port is placed subcutaneously, the ingrowth guard prevents any tissue from growing into the recesses between the catheter and/or catheter lock 50 and the port body stem cover 250. Accordingly, when the port is removed, the catheter 50, ingrowth guard 270, and optionally the stem 230 can be removed to provide a clean surface with which the placement tool 700 can engage. Without the ingrowth guard 270 in place, tissue growth can obstruct the protrusions 254, detents 256, sockets 258, or combinations thereof and prevent the placement tool 700 from engaging the port 208, 210.

FIGS. 3A-G show embodiments of an implantable access port 310. Similar to embodiments described herein, the port 310 includes a port housing 312, a port body 314 including a tunneling edge 366 to facilitate implantation, and a needle penetrable septum 316, including palpation features 326. The housing 312 defines a reservoir 322 bounded by the needle-penetrable septum 316 and includes a stem 330. The stem 330 configured for engaging a catheter 50 and providing fluid communication between the reservoir 322 and the catheter 50.

As shown in FIGS. 3A-G embodiments of the port 310 define a low-profile so that a minimum horizontal length or width of the port 310 is greater than the maximum vertical height of the port 310. Typical power injection ports define a substantially higher profile in order to provide a sufficiently strong septum and tall enough reservoir. By contrast, embodiments described herein define a substantially lower profile for a similar overall footprint.

As shown in FIGS. 3A, 3C, 3E, the footprint of the port 310 can vary in shape including circular e.g. port 310A, crescent shape or a reniform 'kidney bean' shape, e.g. 310B, 310C. It will be appreciated that other shapes of port footprint are also contemplated including triangular, trapezoid, hexagon, polygon, and the like. Embodiments of port 310 also define a substantially flat underside and a continuous, smooth, rounded upper side. These profile shapes allow the port 310 to define a relatively smooth, unobtrusive shape and reduces tissue stress points on an exterior of embodiments of the port 310. Further, the profile of the body 314 minimizes tension on the subcutaneous tissue pocket and sutures that close the post-insertion incision, this in turn minimizes the formation of scar tissue.

FIG. 3A shows an incision line 60 through which port 310A is inserted subcutaneously. When the incision 60 is closed behind the port 310A, the circular footprint and rounded upper surface minimizes the area of stress points 70 on the incision 60, thereby minimizing the formation of scar tissue. Further, the circular footprint allows the port 310A to be eased through an incision that is less than the maximum width of the port 310A itself, thereby allowing for a smaller incision site 60.

FIG. 3C shows port 310B with a crescent shape, or reniform "kidney bean" shape footprint including a convex tunneling portion 360, first and second lobes 336, 338, and a concave stem-side portion 362. A stem 330 extending from the stem-side portion 362, along a longitudinal axis. In an embodiment, a tunneling edge 366 can be sharpened and extends from a first side, proximate a first lobe 336, through to a second side, proximate a second lobe 338. The incision 60 required to insert the port 310B subcutaneously can be shorter than the lateral width of the port 310B and the same length as a longitudinal length (y) of the port 310 that extends along a longitudinal axis between the stem-side portion 362 at the base of the stem 330, and the tunneling portion 360.

As shown in FIG. 3H, positioning the port 310B subcutaneously includes inserting the port 310B sideways with the first lobe 336 passing through the incision 60 first. The port 310B is then inserted by rotating through substantially 900 about a transverse axis until a second lobe 338 passes through the incision 60. As the port 310 is rotated about the transverse axis, the sharpened tunneling edge 366 facilitates separation of the tissue thereby forming a tissue pocket. Once placed subcutaneously, the stress points 70, adjacent the first and second lobes 364, 368 are positioned away from a mid-point of the incision 60 and closer to the end points of the incision 60, diverting any stress on the incision sutures away from the relatively weaker mid-point of the incision 60. In an embodiment, the incision 60 is formed by a scalpel. In an embodiment, the tunneling edge 366 can include a blade to nick the skin and form the incision 60. In an embodiment the blade is retractable.

FIG. 3E shows port 310C with an extended crescent shape, or 'kidney bean' shape footprint including a convex tunneling portion 360, first and second lobes 336, 338, and a concave stem-side portion 362. The stem 330 extending along a longitudinal axis from the stem-side portion 362. In an embodiment, a tunneling edge 366 can extend from a first side through to a second side. The incision 60 required to insert the port 310C subcutaneously can be shorter than the lateral width of the port 310C and the same length as a longitudinal length (y) of the port extending along a longitudinal axis from the stem-side portion 362, at the base of the stem 330, through to the tunneling portion 360.

As shown in FIG. 3H, positioning the port 310C subcutaneously includes inserting the port 310C sideways with the first lobe 336 passing through the incision 60 first. The port 310C is then inserted by rotating through substantially 90° about a transverse axis until a second lobe 338 passes through the incision 60. As the port 310C is rotated about the transverse axis, the sharpened tunneling edge 366 facilitates separation of the tissue forming a tissue pocket. Further, the stress points 70, adjacent the first and second lobes 364, 368 are positioned away from the incision 60, reducing any stress on the incision sutures and reducing the formation of scar tissue.

FIG. 3G shows an embodiment of port 310D including an elongate balloon shaped footprint. Similar to port 310A, port 310D includes rounded edges to facilitate passing through an incision 60, the incision 60 extending laterally the same or slightly less than the lateral width of the port. 310D. Advantageously, the shape of port 310D provides a larger target area with which to access the port and yet does not require any larger of an incision 60. Further the larger target area allows an access needle to be inserted at an acute angle to the skin surface, as discussed in more detail herein.

As shown in FIGS. 3B, 3D, 3F, the septum 316 defines a convex profile when viewed from a side view. As shown in FIG. 3B, the convex septum 316 allows an access needle 40, such as a Huber-type, non-coring needle, to pass through the septum 316 at an acute angle relative to a skin surface 20 of the patient and access the reservoir 322 therebelow. In an embodiment, the access needle can pass through the septum at an angle of 90° or less relative to a horizontal plane of the port 310. Further, the angled entry position allows the entire opening of the needle lumen to remain within the reservoir 322 even if the transverse depth of the reservoir 322 is shorter than a maximum width (x) of the needle bevel 42. Advantageously, this allows the port 310 to define a lower profile than typical ports while still enabling the entire needle bevel 42 to fit within the reservoir 322.

Figures 4A, 4B, 4C, 4D:
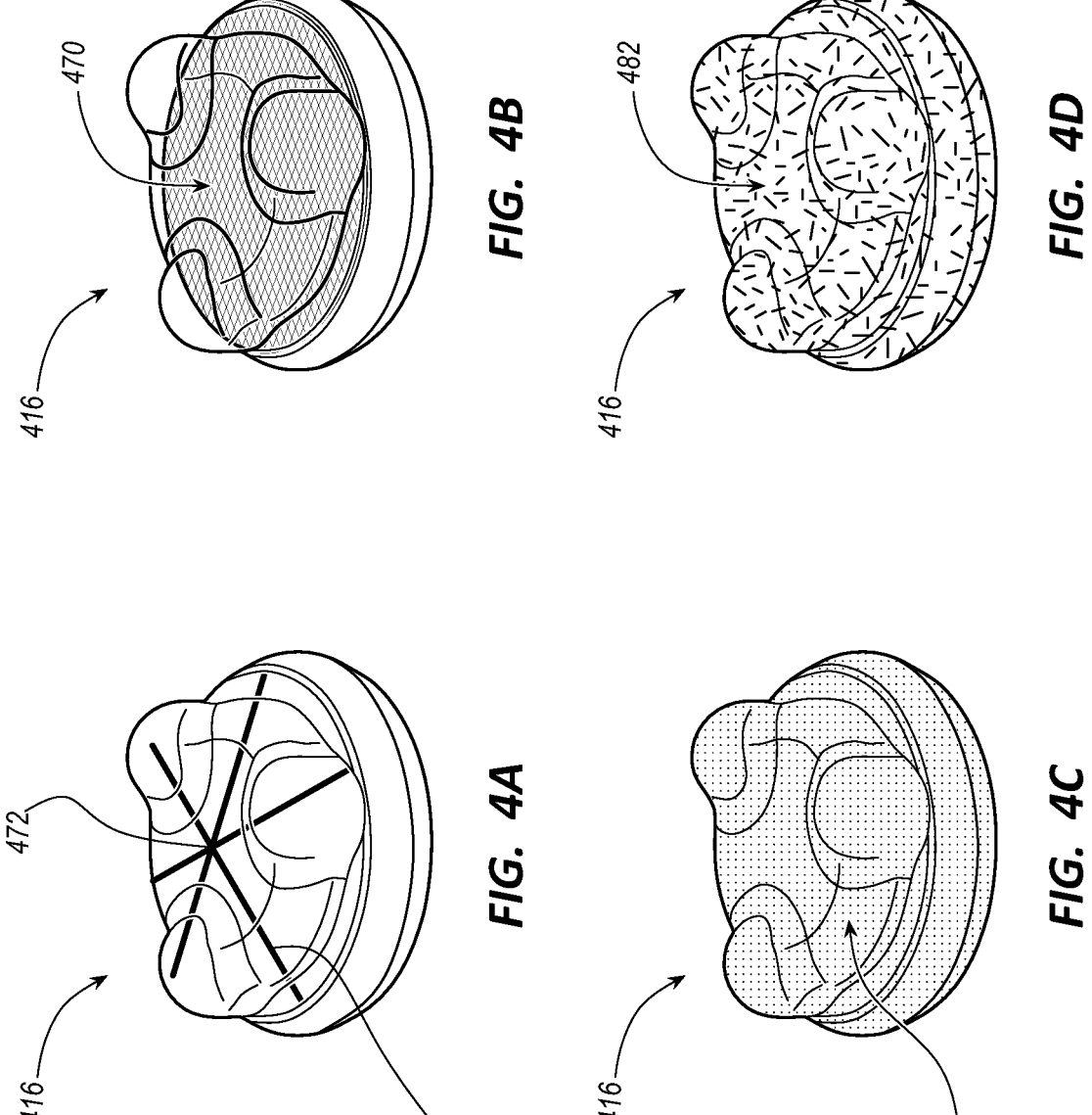

As shown in FIGS. 4A-4B, in an embodiment a septum 416 can include reinforcements such as wires, particles, or combinations thereof. It will be appreciated that any of septa 116, 216, 316 can also include reinforcements described herein. In an embodiment, the reinforcements can include one or more wires 470 extending through the septum 416. The wires can be formed of metal such as titanium or stainless steel, polymers such as nylon, ceramics, or any suitable material. The wires 470 can extend from a first side to a second side, and at least one of the wires 470 can pass through a center-point 472 of the septum 416. In an embodiment, as shown in FIG. 4B, the wires 470 form a mesh structure extending through the septum 416. The openings between the individual strands of wires 470 are sufficient to allow an access needle 40 to pass therebetween. In an embodiment, the septum 416 can be formed by overmolding needle penetrable silicone rubber over the wires 470.

In an embodiment, the septum 416 includes particles 480 to create a reinforced composite material. The particles 480 can include metal, ceramics, polymers, or combinations thereof. The particles 480 can range in size from 10 nm to 1.0 mm in diameter, and are disposed within a matrix of silicone rubber to form the septum 416. In an embodiment, the septum 416 includes filaments 482 to create a reinforced composite material. The septum 416 can include a matrix of silicone rubber and woven or non-woven filaments 480 disposed therein. The filaments can be between 1 mm and 15 mm in length and formed of metal, ceramics, polymers, or combinations thereof.

Advantageously, the reinforcements of the septum 416 allow the septum 416 to define a thinner transverse height while maintaining the ability to withstand typical power injection pressures. Further, the reinforcements can also define a septum with a convex profile, as described herein. Accordingly, a port including the reinforced septum 416 can define a lower profile, reducing stress placed on the surrounding tissue.

FIGS. 5A-D depicts various details of an implantable access port placement tool ("placement tool" or "tool"), generally designated at 500, according to an embodiment. As shown, the tool 500 includes an elongate body 514 extending between a distal end 560 and proximal end 562. A proximal portion of the body defines a handle 516 for grasping of the tool. The handle can further include a grip surface 518 to assist the grasping of the tool 500.

The tool 500 further includes a port holder 510 disposed at a distal end 560 of the tool 500. The port holder 510 is configured to releasably hold an access port 30 prior to its placement in a subcutaneous tissue pocket defined in the placement tool 500. It will be appreciated that port 30 can include any of the port embodiments 110, 210, 310 disclosed herein as well as other generic access ports.

The port holder includes a base 540 defining a flat underside and an elliptical perimeter 528 extending from a first side, to a distal end 560, to a second side. The footprint of the elliptical perimeter 528 substantially matches the footprint of a port 30. Extending from the elliptical perimeter 528 is a panel 524 that defines a cavity 522. The cavity 522 is configured to receive a portion of the access port 30. The panel 524 is angled in a proximal direction and curved to match the elliptical perimeter 528. As shown in FIG. 5B, a side profile of the panel 524 extends proximally from the elliptical perimeter 528 to provide a sloping tunneling portion that facilitates dissection of tissue as the placement tool is urged subcutaneously.

In an embodiment, the port holder 510 is sized to match the approximate size of the access port 30, enabling the clinician using the placement tool 500 to insert the port holder into a subcutaneous pocket and determine whether the pocket is sufficiently sized to receive the access port 30 prior to insertion. This simplifies the placement of the port 30 for the clinician. It will be appreciated that size, shape and configuration of the port holder 510, the base 540, the curved panel 524, or combinations thereof, can vary in order to receive different sizes, shapes and configurations of port 30. In an embodiment, a portion of the elliptical perimeter 528 can be sharpened to provide a sharpened tunneling edge 566. The tunneling edge 566 can be used to separate the tissue of the patient and define the subcutaneous tissue pocket into which the access port 30 will be placed. In an embodiment, a portion of the elliptical perimeter 528 includes a blade for nicking the skin and forming an incision. In an embodiment, the blade is formed of separate material from the tool 500, or port holder 510 and is selectively retractable.

Advantageously, the tool 500 provides a single instrument within which to create an incision, separate the subcutaneous tissues to create a tissue pocket, size the tissue pocket to match the size of the port, and place the port within the tissue pocket, or combinations thereof. A procedure that previously required a scalpel to create an incision, a Kelly clamp to separate the tissues, and repeated insertion of the port until the tissue pocket is of the correct size. Further, the tool 500 provides an instrument that performs the incision, separation, sizing and placing of the port 30, or combinations thereof, in a single action.

As shown in FIG. 5D, in an embodiment, the port holder includes a first and second curved panel arms 524A, 524B. Each of panel arms 524A, 524B engage along a longitudinal axis to define a profile substantially the same as panel 524. Each of first and second curved panel arms 524A, 524B are hingedly connected to the port holder 510 at a side portion and rotate thereabout along a horizontal plane. The first and second curved panel arms 524A, 524B can also be operably connected to an actuator 530 located on the handle 516. In use, with a port 30 placed within a tissue pocket, a clinician can selectively release the port 30 from the port holder 510 by actuating the actuator 530 which causes the first and second curved panel arms 524A, 524B to open and release the port 30. The tool 500, along with port holder 510 can then be removed proximally while leaving the port 30 in place.

In an exemplary method of inserting an access port subcutaneously, a port is provided such as is discussed in embodiments herein. The port can be coupled to a distal end of a placement tool, for example tool 500. In an embodiment, the placement tool 500 includes a port holder 510 that includes a recess 522. The port engages the recess of the port holder and is secured thereto. The placement tool further includes a sharpened tunneling edge 566 and a sloped profile to facilitate formation of a tissue pocket as the tool is urged subcutaneously.

In an embodiment, an incision is formed either by using a scalpel, or by using the tunneling edge 566 of the placement tool 500 that includes a blade, the tool is then urged subcutaneously. The sharpened tunneling edge and sloped profile of the panel simultaneously dissects the tissue to form a tissue pocket and sizes the pocket to fit the port. In an embodiment the placement tool is then withdrawn and the port is then placed within the tissue pocket. In an embodiment, the port is coupled with the port holder 510 prior to subcutaneous placement of the tool 500. With the port placed subcutaneously, the user actuates an actuator mechanism 530 which causes the panel arms 524A, 524B to rotate outwards and release the port from the distal end of the placement tool 500. The placement tool 500 can then be withdrawn.

In an embodiment, as shown in FIG. 5E, the placement tool 502 includes an elongate body 514 extending between a distal end 560 and a proximal end 562. A proximal portion of the body 514 defines a handle 516 for grasping of the tool. The handle can further include a grip surface 518 to assist the grasping of the tool 502. The tool 502 further includes a flattened base portion 540 disposed at a distal end 560. The base portion 540 defines an elliptically-shaped tunneling edge 566 that can be sharpened to facilitate tissue dissection and formation of a tissue pocket. Optionally, the tunneling edge 566 can include a blade for nicking the skin and forming an incision. As shown in FIG. 5E, a plan view of the base portion 540 shows the base 540 defining a footprint that substantially matches the footprint of a port 30. It will be appreciated that the shape of the base portion 540 can vary to match the shape of the port footprint it is configured to insert.

In use, the placement tool 502 is grasped by the clinician and urged subcutaneously. In an embodiment, the tool 502 includes a blade to nick the skin and form an incision, through which the tool 502 is then urged. In an embodiment, the incision is formed by a scalpel. The tool 502 is then urged subcutaneously to dissect the tissue until the entire base portion 540 is disposed within the patient. Since the shape of the base portion 540 is the same, or slightly larger than a footprint of the port 30 to be inserted, the tool 502 defines a tissue pocket of a suitable size and depth. The placement tool 502 can be withdrawn and the port 30 can be disposed within the tissue pocket. It will be appreciated that port placement can be performed with or without a catheter 50 coupled to the port 30. In an embodiment the placement tools 500, 502 are formed of metal, polymer, plastic, or any suitable rigid material, or combinations thereof. For example, the tool body 514 can be formed of a polymer and include a metallic tunneling edge 566. These and similar combinations are contemplated to fall within the scope of the present invention.

As shown in FIG. 6, an embodiment of a placement tool 600 is disclosed. The placement tool 600 includes a first arm 612 extending from a proximal end to a distal end, and a second arm 614 also extending from a proximal end to a distal end. The first and second arms 612, 614 are hingedly connected at a mid-portion 616. A proximal end of each of the first and second arms 612, 614 include a finger loop 618, or similar structure to allow the clinician to grip each of the first and second arms 612, 614 with a finger or thumb. The tool 600 further includes a latch 620 disposed between the first and second arms 612, 614 and designed to lock the first and second arms 612, 614 in one or more closed positions. As shown, the latch 620 is disposed towards a proximal end, although other configurations are contemplated.

A distal end of the first and second arms 612, 614 each include a port holder 610, e.g. first and second port holder 610A, 610B. The port holder 610 is configured to receive a side portion of a port 30. In an embodiment, the port holder includes a curved loop shaped to receive a lobe of the port body although it will be appreciated that the shape of the port holder 610 can vary to fit different shaped ports.

A distal end of the first arm 612, the second arm 614, or combinations thereof also include a blade 640. The blade 640 extends distally from a distal end of the port holder 610. The blade 640 can define a crescent shape that extends around and in front of a port 30 disposed within the port holder. The blade, 640 can include a sharpened distal edge for forming an incision and dissecting tissue. In an embodiment, both the first and second arms 612, 614 each include a blade 640, e.g. first and second blades 640A, 640B, which engage at a lateral mid-point when the placement tool 600 is in one or more closed positions. In an embodiment each of the blades 640A, 640B can slide over each other in a scissor-like action as the finger loops are moved toward and apart from each other by the clinician.

In an exemplary method of use, the placement tool 600 can secure a port 30 between each of the port holders 610A, 610B. A user can close the port holder 610 about the port 30 by moving the finger loops 618 toward each other until the latch 620 engages and locks the placement tool 600 in a closed position. The clinician can then urge the placement tool subcutaneously, by using the blade 640 to form an incision. The clinician continues to urge the placement tool 600 subcutaneously to dissect the tissue and form a tissue pocket. When the port 30 is placed, the clinician can unlock the latch 620 and move the finger loops 618 apart to release the port 30. The placement tool 600 can then be withdrawn. It will be appreciated that port placement can be performed with or without a catheter 50 coupled to the port 30. In an embodiment the placement tool 600 is formed of metal, polymer, plastic, or any suitable rigid material, or combinations thereof. For example, the first and second arms 612, 614 can be formed of a polymer and include a metallic sharpened blade 640 disposed therein. These and similar combinations are contemplated to fall within the scope of the present invention.

FIG. 7 shows an embodiment of a placement tool 700. The placement tool 700 includes an elongate body 714 extending between a distal end 760 and proximal end 762. A proximal portion of the body defines a handle 716 for grasping the tool. A distal portion of the tool 700 further includes a port holder 710. The port holder 710 is configured to releasably secure an access port 30, for example ports 110, 210, prior to placement in a subcutaneous pocket defined in the body of a patient.

The port holder 710 includes mechanisms for securing the port holder 710 to the port, for example to the stem cover 150. The mechanisms include various latches, protrusions, abutments, detents, connectors, and the like, for releasably securing the port holder 710 to the port stem cover 150. The handle 716 includes an actuator 730 that is operably connected to mechanisms within the port holder 710. In use, a clinician can actuate the actuator 730 to selectively release the stem cover 150 from a distal connecting portion 760 of the port holder 710. The placement tool 700 further includes a safety clip 770 to prevent premature release of the port 30 from the tool 700.

In an exemplary method of inserting an access port subcutaneously, a port is provided such as is discussed in embodiments herein. The port can be coupled to a distal end of a placement tool, e.g. tool 700 in an embodiment, the placement tool engages a stem cover. In an embodiment the placement tool engages an outer surface of the stem cover and the port is coupled to the catheter prior to insertion. In an embodiment, the placement tool engages an inner surface of the stem cover, an end surface of the stem cover, a stem aperture 234, or combinations thereof. The catheter 50 and stem portion 230 are engaged with the port after subcutaneous insertion. The port further includes a tunneling edge and a sloped profile to facilitate formation of a tissue pocket by the port. In an embodiment, an incision is formed by either using a scalpel, or by using a sharpened edge of the port. The port is then urged subcutaneously using the placement tool. The tunneling edge and sloped profile of the tunneling portion of the port simultaneously dissects the tissue to form a tissue pocket as well as sizes the pocket to fit the port. With the port placed subcutaneously, the user actuates an actuator mechanism which releases the port from a distal end of the placement tool.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A subcutaneous access port system, comprising:
   a placement tool including a proximal handle and a port holder disposed distally; and
   an implantable access port releasably secured to the port holder, the implantable access port comprising:
   a housing including a base, a reservoir, and a stem aperture extending longitudinally through the base and communicating with the reservoir;
   a needle-penetrable septum covering the reservoir; and
   a body coupled to the housing over the needle-penetrable septum, the body comprising:
   a stem cover extending longitudinally from an outer surface of the body in a stem-wards direction, the port holder configured to engage the stem cover;
   a tunneling portion having a tunneling edge opposite of the stem cover designed to dissect tissue as the implantable access port is urged subcutaneously, a longitudinal cross-sectional shape of the tunneling portion defining a sigmoid profile having a concave hollow disposed between the tunneling edge and the reservoir;
   a skive extending linearly from a lateral outer-most point disposed stem-wards of a transverse central axis of the needle-penetrable septum, to the tunneling edge to define a tapered footprint; and
   wherein the port holder directly engages an inner surface of the stem cover to releasably secure the implantable access port to the placement tool.

2. The subcutaneous access port system according to claim 1, further comprising an indicia marker, the indicia marker disposed between the base and the body.

3. The subcutaneous access port system according to claim 2, wherein the indicia marker is radiopaque and includes one of an alphanumeric symbol and shape denoting one of a feature and an orientation of the implantable access port.

4. The subcutaneous access port system according to claim 1, wherein the placement tool engages an outer surface of the stem cover.

5. The subcutaneous access port system according to claim 1, wherein the stem aperture is configured for receiving a stem portion, the stem portion providing fluid communication between the reservoir and a catheter attached thereto.

6. The subcutaneous access port system according to claim 1, wherein the stem cover includes one of a protrusion, a detent, and a socket, configured to engage the placement tool.

7. The subcutaneous access port system according to claim 1, wherein the body includes a first skive on a first side surface thereof, and a second skive on a second side surface thereof, opposite the first side surface, the first skive and the second skive defining the tapered footprint of a distal portion of the body.

8. The subcutaneous access port system according to claim 1, wherein the needle-penetrable septum defines a convex upper surface to allow a needle to access the reservoir at an acute angle relative to a skin surface of a patient.

9. The subcutaneous access port system according to claim 1, wherein a vertical depth of the reservoir is less than a maximum length of a bevel of an access needle, accessing the implantable access port.

10. The subcutaneous access port system according to claim 1, wherein a footprint shape of the implantable access port includes one of a circular, crescent, reniform, an elongate balloon, and an arrow shape.

11. The subcutaneous access port system according to claim 1, wherein the needle-penetrable septum includes a reinforcement.

12. The subcutaneous access port system according to claim 11, wherein the reinforcement includes one of a wire reinforcement and a matrix reinforcement.

13. The subcutaneous access port system according to claim 11, wherein the reinforcement includes a wire mesh.

14. The subcutaneous access port system according to claim 11, wherein the reinforcement includes a plurality of individual wire strands, and wherein a strand of the plurality of individual wire strands extends through a center-point of the needle-penetrable septum.

15. The subcutaneous access port system according to claim 11, wherein the reinforcement includes a matrix of silicone rubber with one of a plurality of particles and a plurality of fibers disposed therein.

16. The subcutaneous access port system according to claim 15, wherein the plurality of particles are formed of one of a metal, a ceramic, and a polymer, and the plurality of particles range in size from 10 nm to 1.0 mm in diameter.

17. The subcutaneous access port system according to claim 15, wherein the plurality of fibers are formed of one of a metal, a ceramic, and a polymer, and wherein the plurality of fibers range in length from between 1 mm to 15 mm.

18. The subcutaneous access port system according to claim 1, wherein the tunneling edge is sharpened to facilitate dissection of the tissue as the implantable access port is urged subcutaneously.

19. The subcutaneous access port system according to claim 1, wherein an outer surface of the stem cover extends from the outer surface of the body at an angle relative thereto, the outer surface of the stem cover extending parallel to a central axis of the stem aperture.

20. The subcutaneous access port system according to claim 1, wherein the port holder includes an engagement mechanism and the proximal handle includes an actuator operably coupled to the engagement mechanism, the actuator configured to actuate the engagement mechanism to release the stem cover from the port holder.

21. The subcutaneous access port system according to claim 20, further including a safety clip releasably coupled to the placement tool and configured to prevent the engagement mechanism from releasing the stem cover when the actuator is actuated.

22. The subcutaneous access port system according to claim 1, wherein an outer-most lateral diameter and an outer-most transverse diameter of the port holder and an elongate body extending between the port holder and the proximal handle is less than an outer-most lateral diameter and an outer-most transverse diameter of the implantable access port, respectively.

* * * * *